US010918414B2

(12) United States Patent
Yang et al.

(10) Patent No.: US 10,918,414 B2
(45) Date of Patent: Feb. 16, 2021

(54) DEVICE, INSTRUMENT AND BELT FOR TYING CERVIX

(71) Applicants: INDUSTRIAL TECHNOLOGY RESEARCH INSTITUTE, Hsin-Chu (TW); Chang Gung Medical Foundation Lin-Kou Chang Gung Memorial Hospital, Tao-Yuan (TW)

(72) Inventors: Chih-Wen Yang, Taoyuan (TW); Po-Jen Cheng, Taipei (TW); Ting-Hsuan Chen, Zhubei (TW); Tseng-Huang Liu, Kaohsiung (TW)

(73) Assignees: INDUSTRIAL TECHNOLOGY RESEARCH INSTITUTE, Hsin-Chu (TW); CHANG GUNG MEDICAL FOUNDATION LIN-KOU CHANG GUNG MEMORIAL HOSPITAL, Tao-Yuan (TW)

( * ) Notice: Subject to any disclaimer, the term of this patent is extended or adjusted under 35 U.S.C. 154(b) by 185 days.

(21) Appl. No.: 16/220,221

(22) Filed: Dec. 14, 2018

(65) Prior Publication Data
US 2019/0183530 A1 Jun. 20, 2019

(30) Foreign Application Priority Data

Dec. 15, 2017 (TW) ................................ 106144244
Nov. 28, 2018 (TW) ................................ 107142412

(51) Int. Cl.
*A61B 17/44* (2006.01)
*A61B 17/12* (2006.01)
(Continued)

(52) U.S. Cl.
CPC ........ *A61B 17/44* (2013.01); *A61B 17/12009* (2013.01); *A61B 17/42* (2013.01); *A61B 90/30* (2016.02); *A61B 2017/4225* (2013.01)

(58) Field of Classification Search
CPC ... A61B 17/44; A61B 17/12009; A61B 17/42; A61B 17/12; A61B 90/30; A61B 2017/4225; A61B 17/12018; A61F 5/0089
See application file for complete search history.

(56) References Cited

U.S. PATENT DOCUMENTS 4,961,436 A  10/1990 Koch
5,807,281 A   9/1998 Welch
(Continued)

FOREIGN PATENT DOCUMENTS

CN  201572125 U  9/2010
CN  201806769 U  4/2011
(Continued)

OTHER PUBLICATIONS

Vanita B. Dharan MD et al., Alternative treatment for a short cervix: the cervical pessary, Seminars in Perinatology, 2009.
(Continued)

*Primary Examiner* — Erich G Herbermann
(74) *Attorney, Agent, or Firm* — Locke Lord LLP; Tim TingkanG Xia, Esq.

(57) ABSTRACT

A device, an instrument and a belt for tying the cervix are provided. The device includes the belt and the instrument. The belt is used to tie the cervix. The instrument includes a first outer pipe, a second outer pipe and two fork structures. The first outer pipe and the second outer pipe are rotatable to each other. The two fork structures are connected individually to corresponding axial ends of the first outer pipe and the second outer pipe, respectively, and insert into the belt detachably.

35 Claims, 27 Drawing Sheets

(51) Int. Cl.
*A61B 17/42* (2006.01)
*A61B 90/30* (2016.01)

(56) References Cited

U.S. PATENT DOCUMENTS

| | | | |
|---|---|---|---|
| 5,980,534 | A | 11/1999 | Gimpelson |
| 7,036,511 | B2 | 5/2006 | Nissenkorn |
| 7,153,280 | B2 | 12/2006 | Welch |
| 8,347,888 | B2 | 1/2013 | Valtchev |
| 8,728,140 | B2 | 5/2014 | Feemster et al. |
| 9,463,044 | B2 | 10/2016 | Pedrick et al. |
| 9,592,078 | B2 | 3/2017 | Ahluwalia |
| 2004/0092847 | A1 | 5/2004 | Welch |
| 2004/0236349 | A1 | 11/2004 | Gellman et al. |
| 2005/0021049 | A1 | 1/2005 | Welch |
| 2007/0142844 | A1 | 6/2007 | Kotmel et al. |
| 2012/0078272 | A1* | 3/2012 | Smith .............. A61B 17/12009 606/140 |
| 2013/0103044 | A1 | 4/2013 | Brown |
| 2017/0087344 | A1 | 3/2017 | Ichim |

FOREIGN PATENT DOCUMENTS

| | | |
|---|---|---|
| CN | 202211746 U | 5/2012 |
| CN | 202920311 U | 5/2013 |
| CN | 205268253 U | 6/2016 |
| CN | 106061418 A | 10/2016 |
| CN | 205626058 U | 10/2016 |
| CN | 205758676 U | 12/2016 |
| CN | 106794029 A | 5/2017 |
| KR | 101716449 B1 | 3/2017 |
| RU | 2017105056 A | 4/2017 |
| WO | 9621392 A1 | 7/1996 |

OTHER PUBLICATIONS

Ben Panko, Common technique to prevent premature birth could actually cause it, 2016.
A computational model of the pregnant occupant: Effects of Restraint Usage and Occupant Position on Fetal Injury Risk, Stefan Duma et al., 19th International Technical Conference on the Enhanced Safety of Vehicles (ESV), 2005.
Adwoa Baah-Dwomoh et al., Mechanical Properties of Female Reproductive Organs and Supporting Connective Tissues: A Review of the Current State of Knowledge, Applied Mechanics Review, ASME, 2016, vol. 68.
M.S. Mancuso, MD et al., Prevention of preterm birth based on a short cervix: cerclage, Semin Perinatol, 2009, 33(5), 325-333.
L.M. Kindinger et al., Relationship between vaginal microbial dysbiosis, inflammation, and pregnancy outcomes in cervical cerclage, Sci Transl Med., 2016.
Taiwan Patent Office, "Office Action", dated Aug. 10, 2018, Taiwan.
China Patent Office, "Office, Action", dated Feb. 3, 2020, China.
Taiwan Patent Office, "Office, Action", dated May 10, 2019, Taiwan.

* cited by examiner

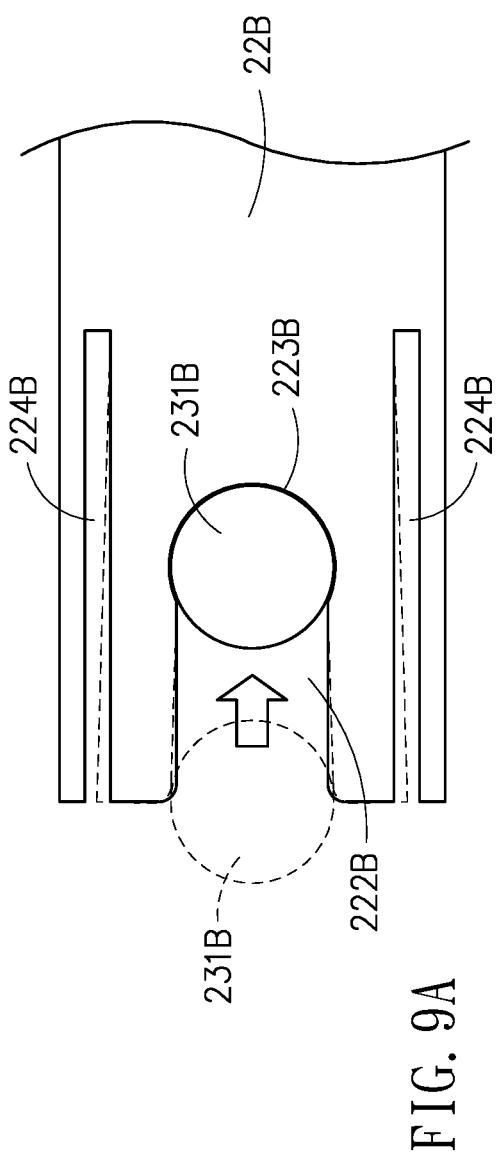
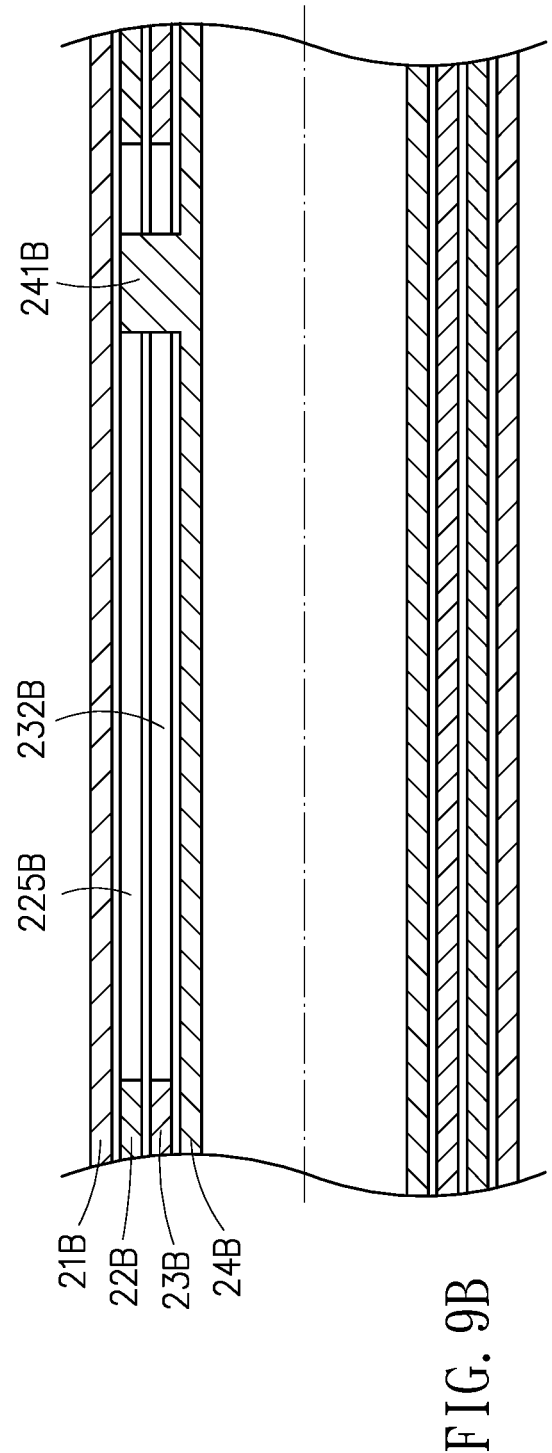
FIG. 9A
FIG. 9B

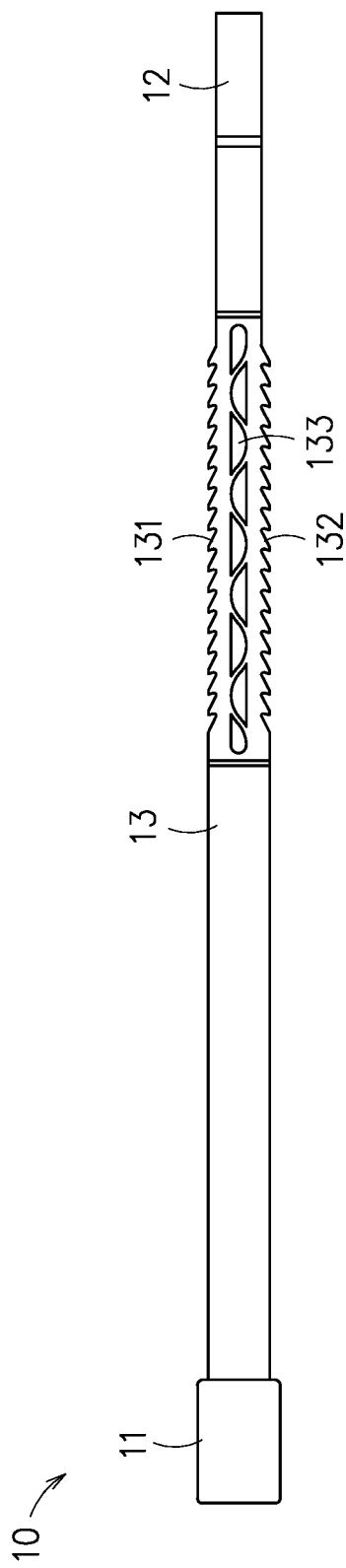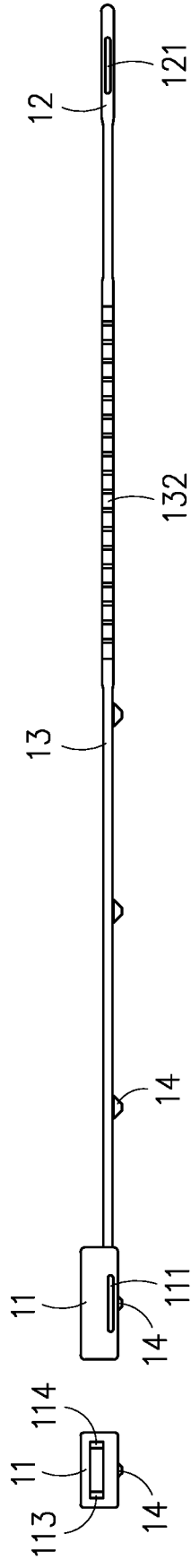
FIG. 15A  FIG. 15B  FIG. 15C

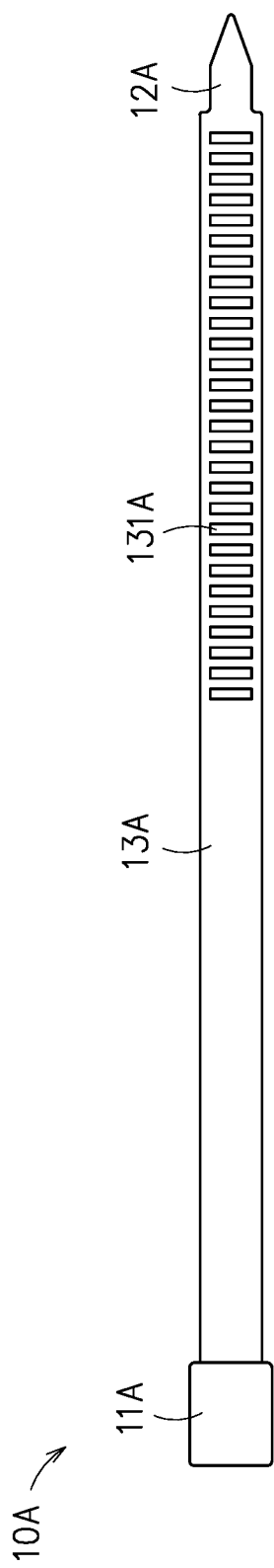
FIG. 21A
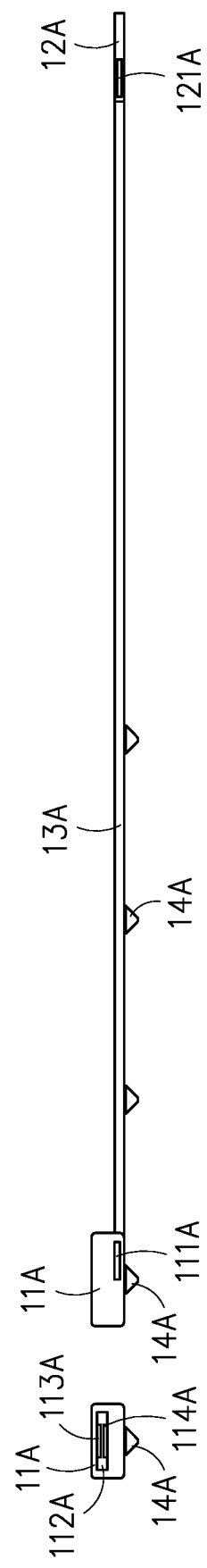
FIG. 21B
FIG. 21C

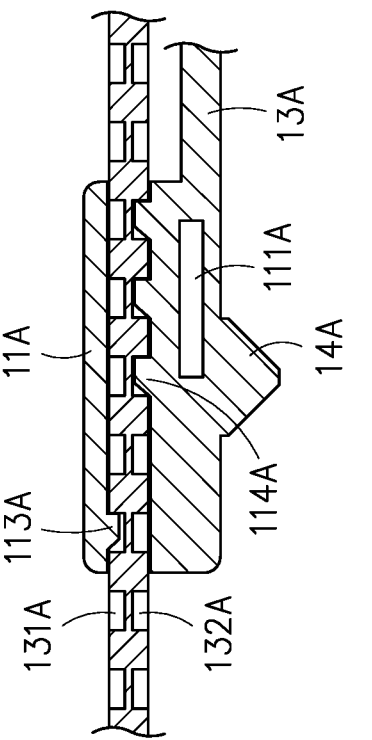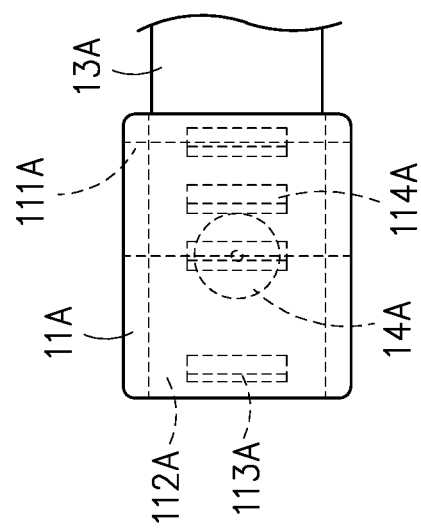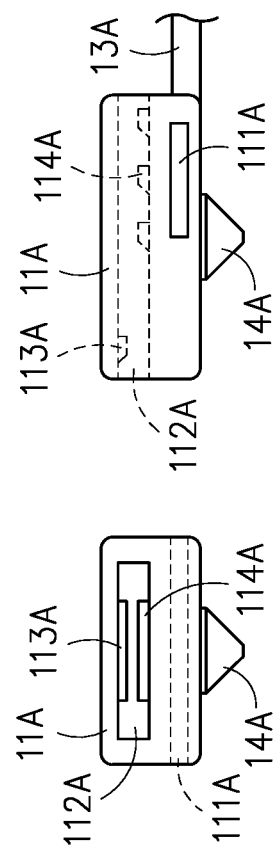

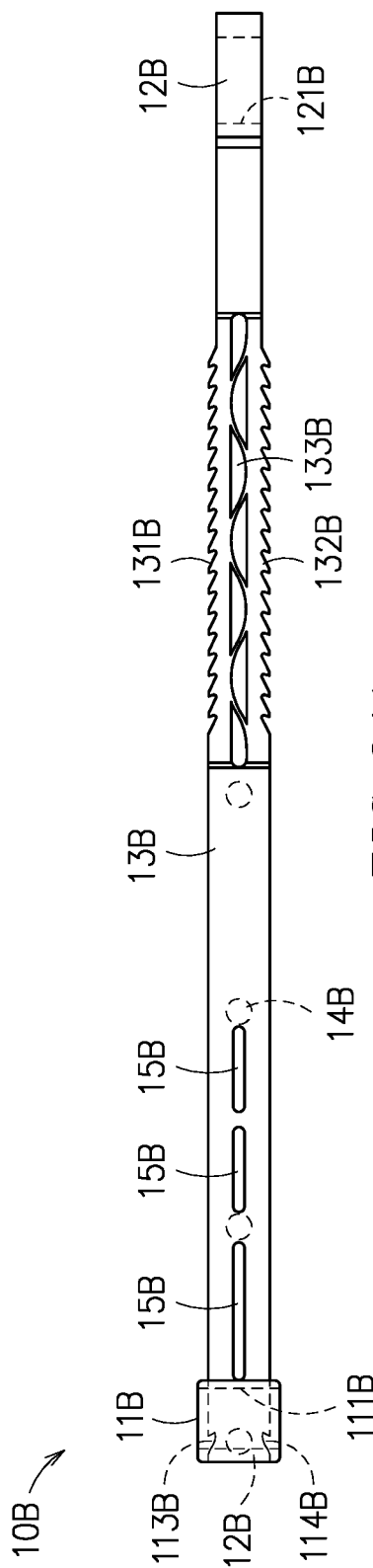
FIG. 24A
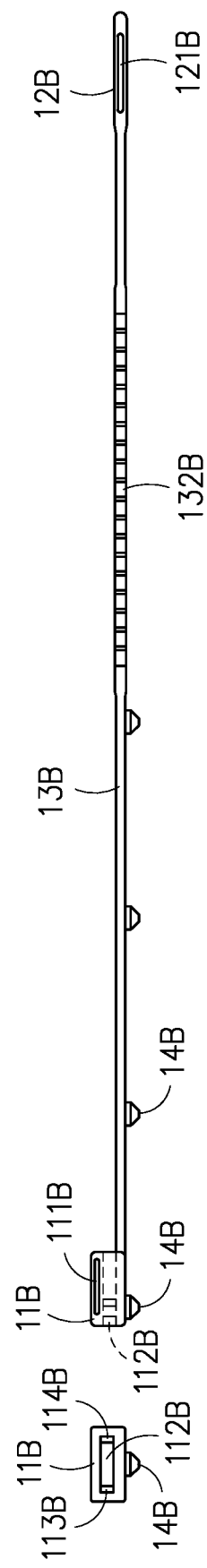
FIG. 24B
FIG. 24C

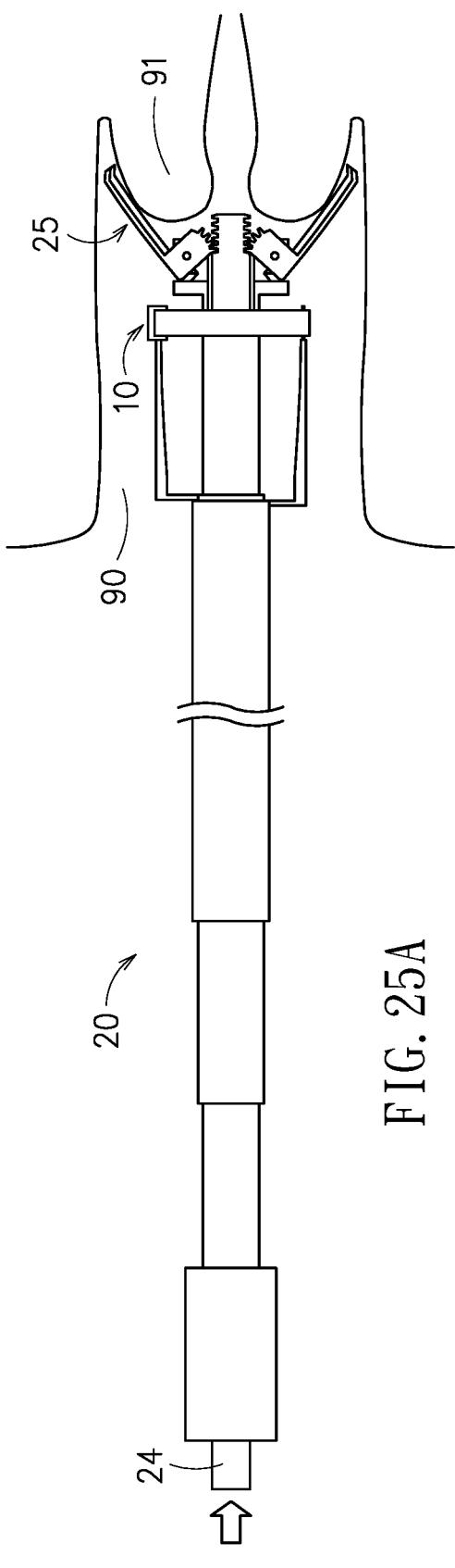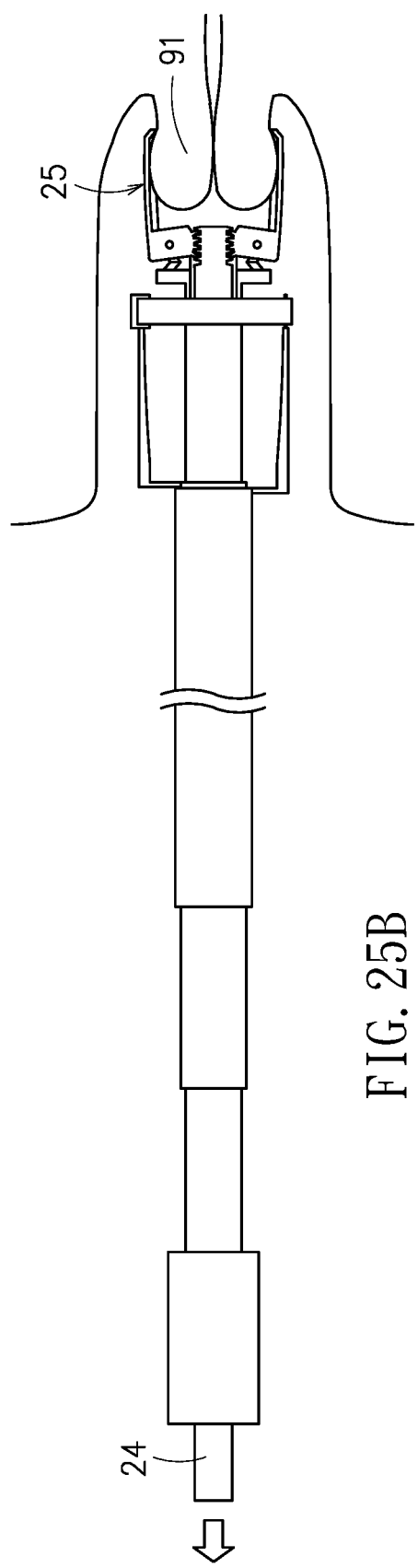
FIG. 25A
FIG. 25B

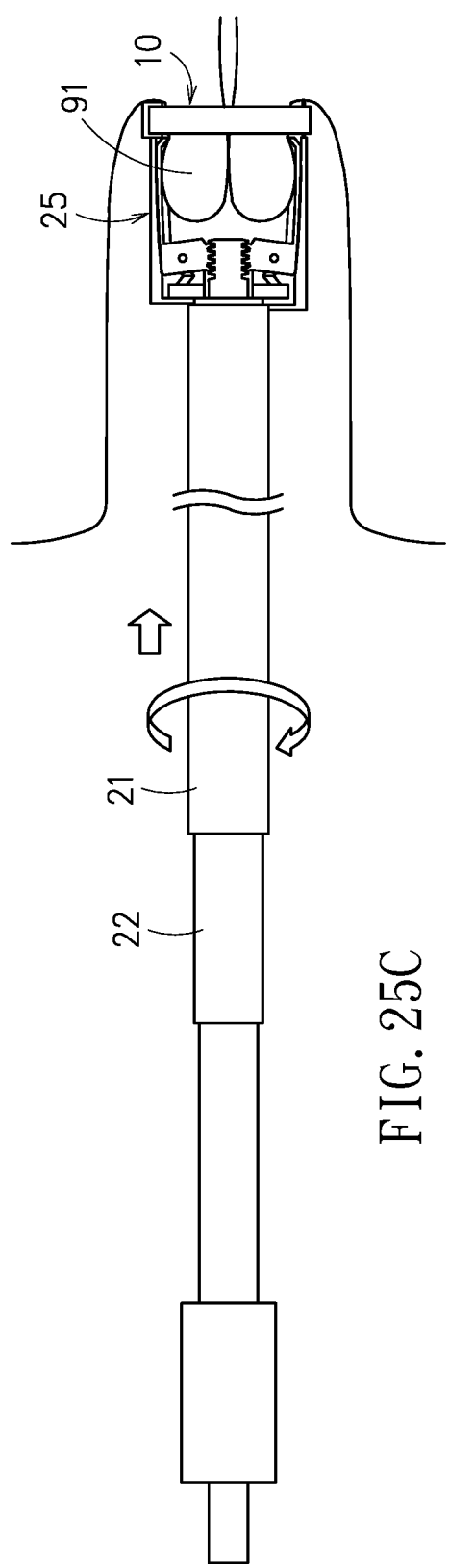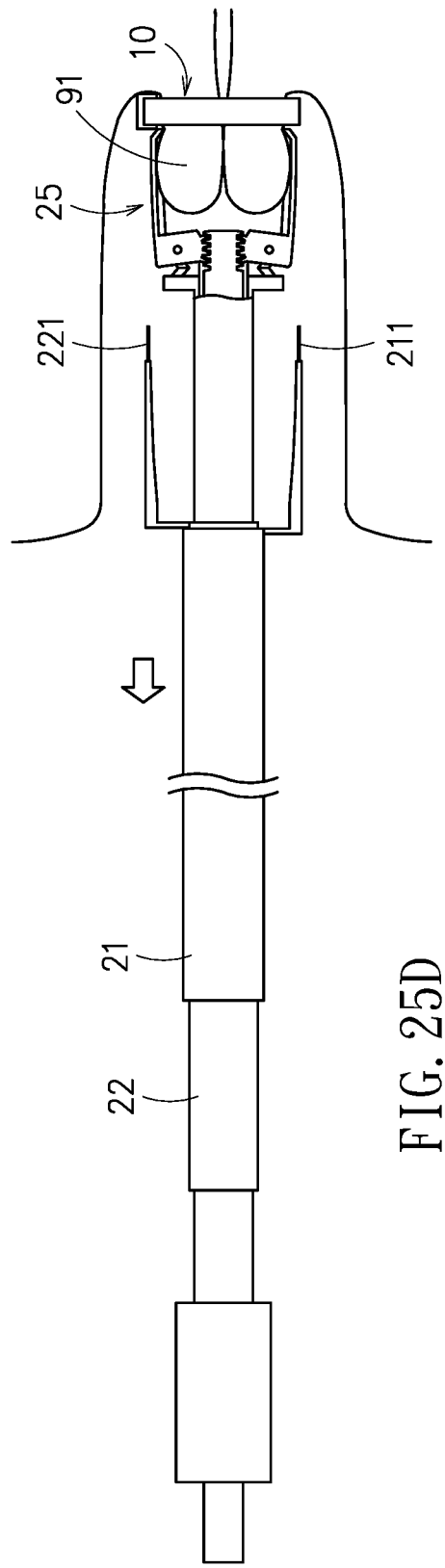

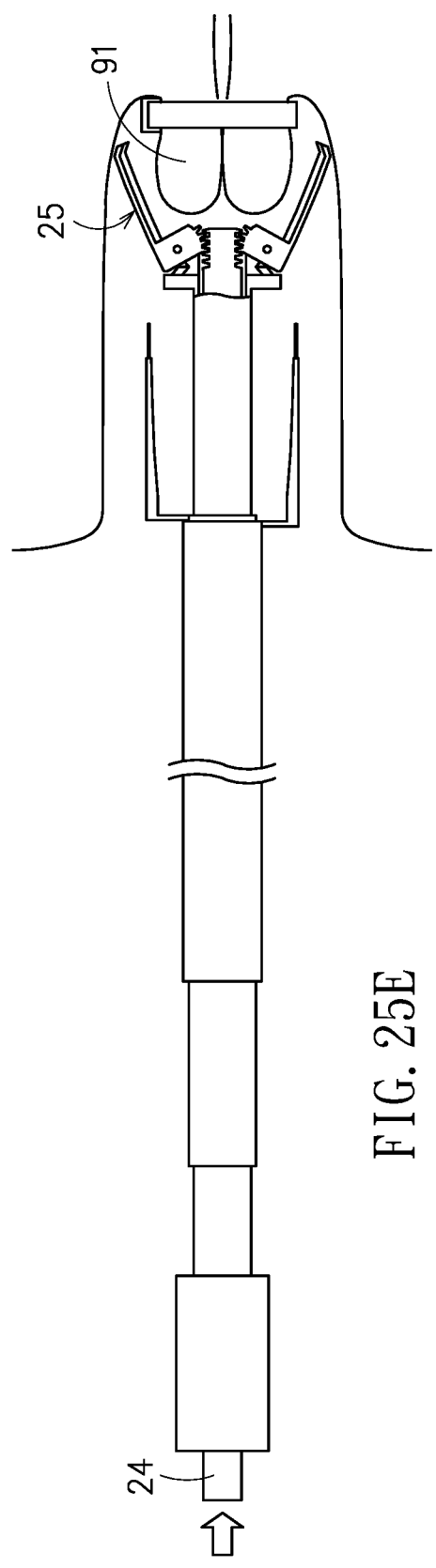
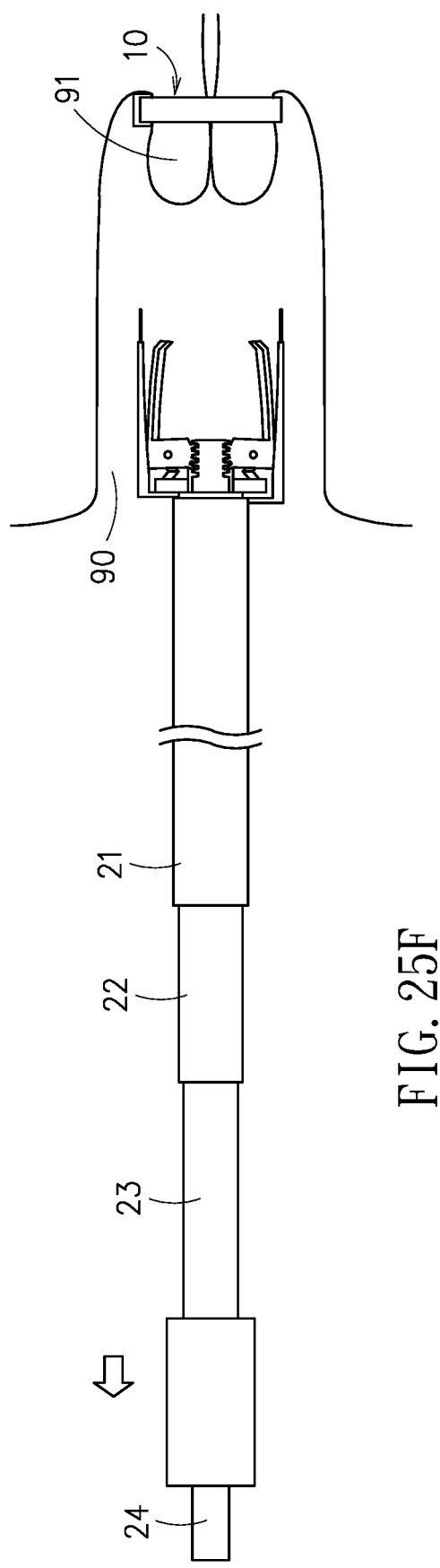
FIG. 25E
FIG. 25F

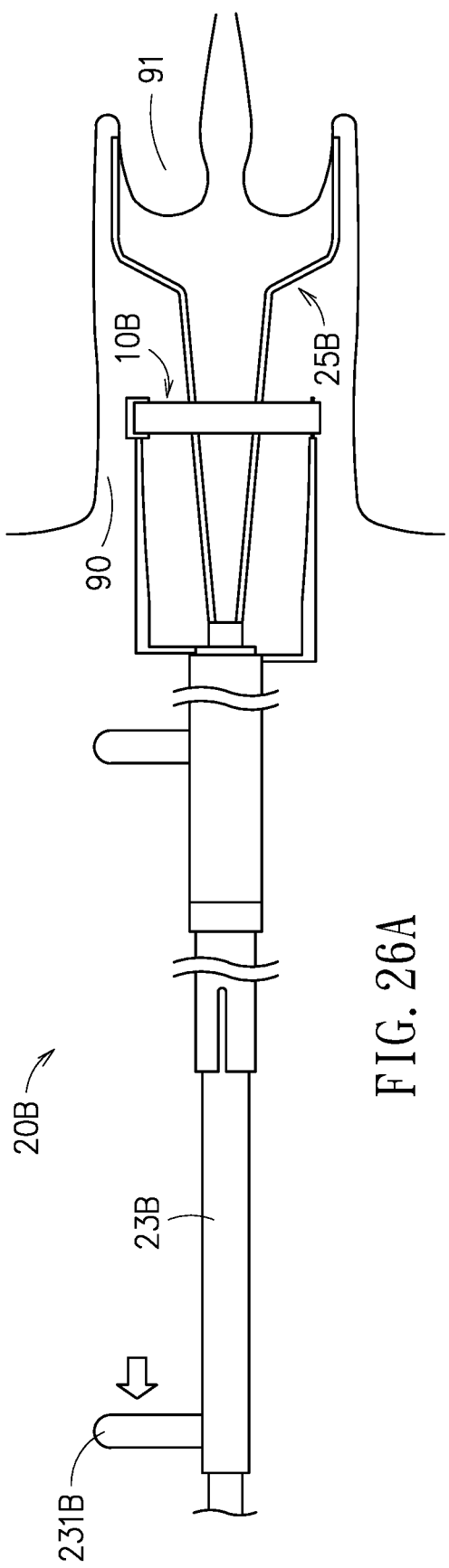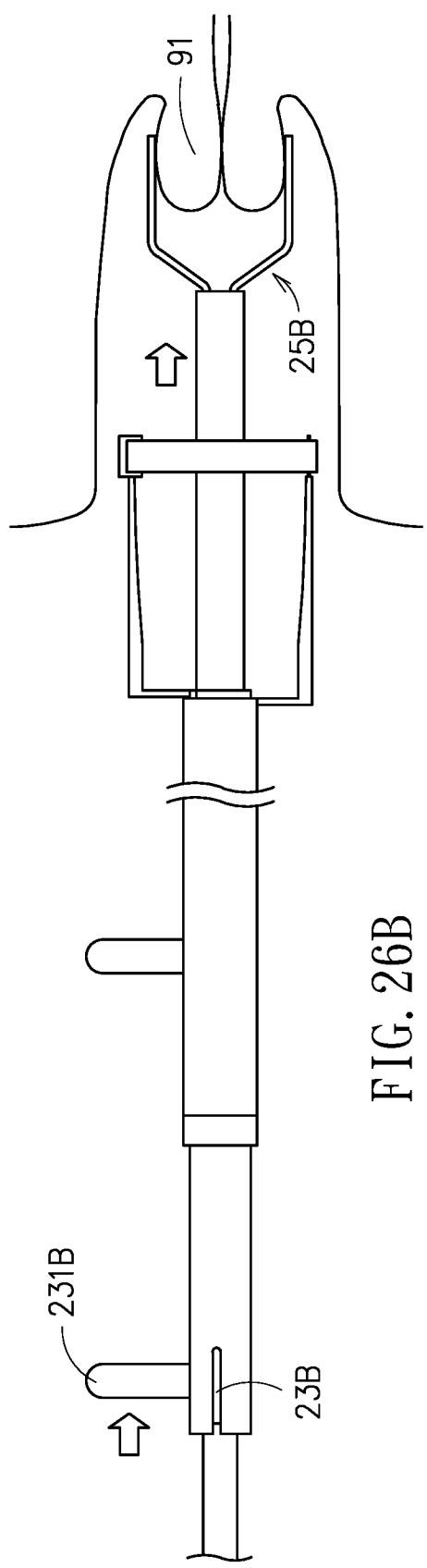
FIG. 26A
FIG. 26B

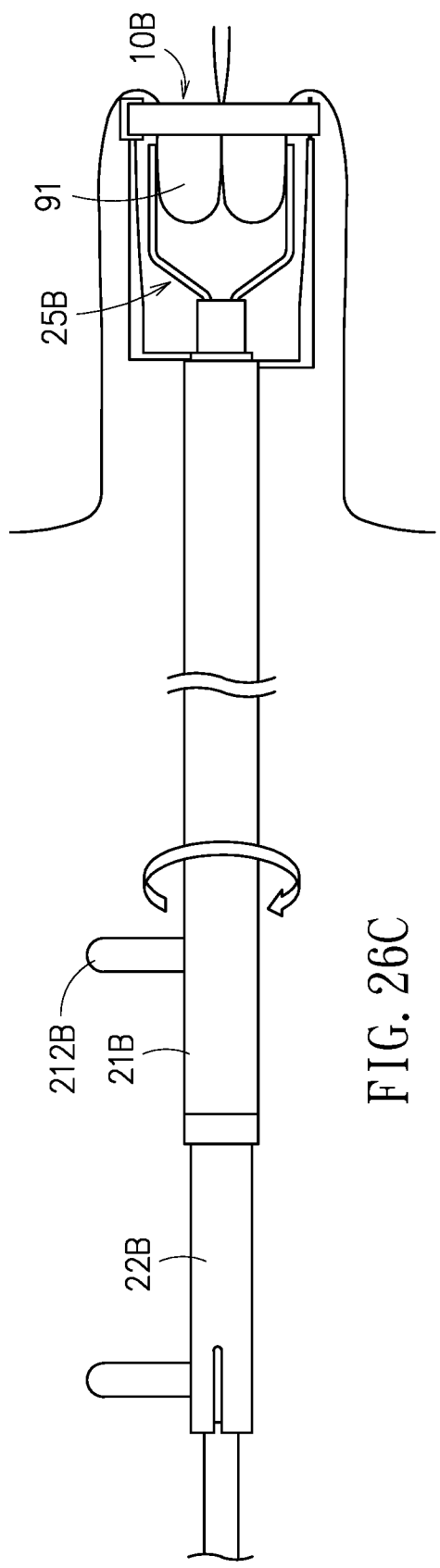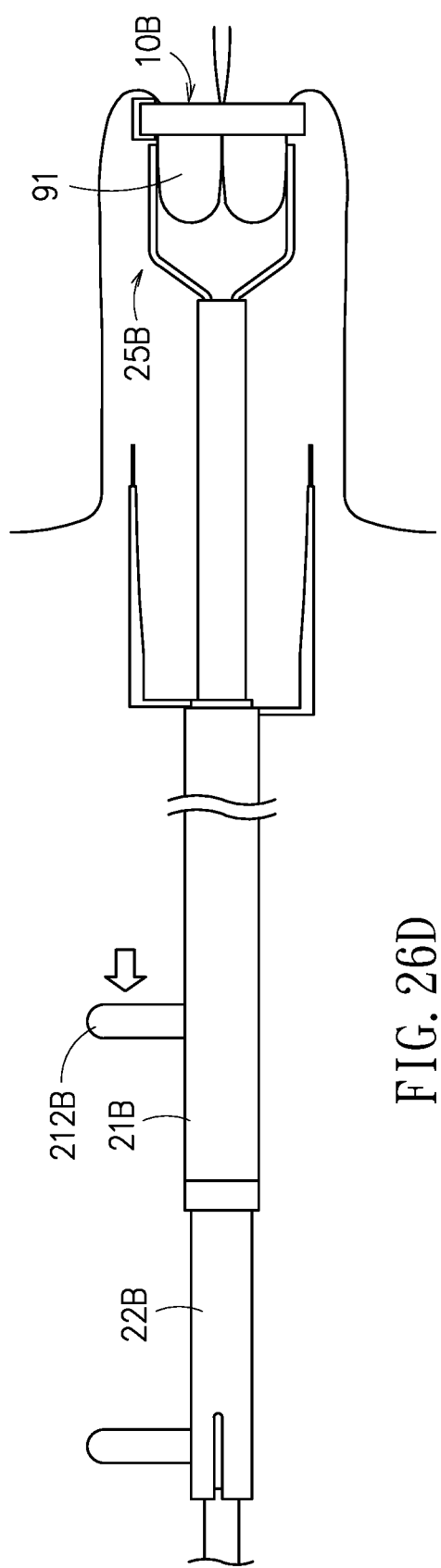

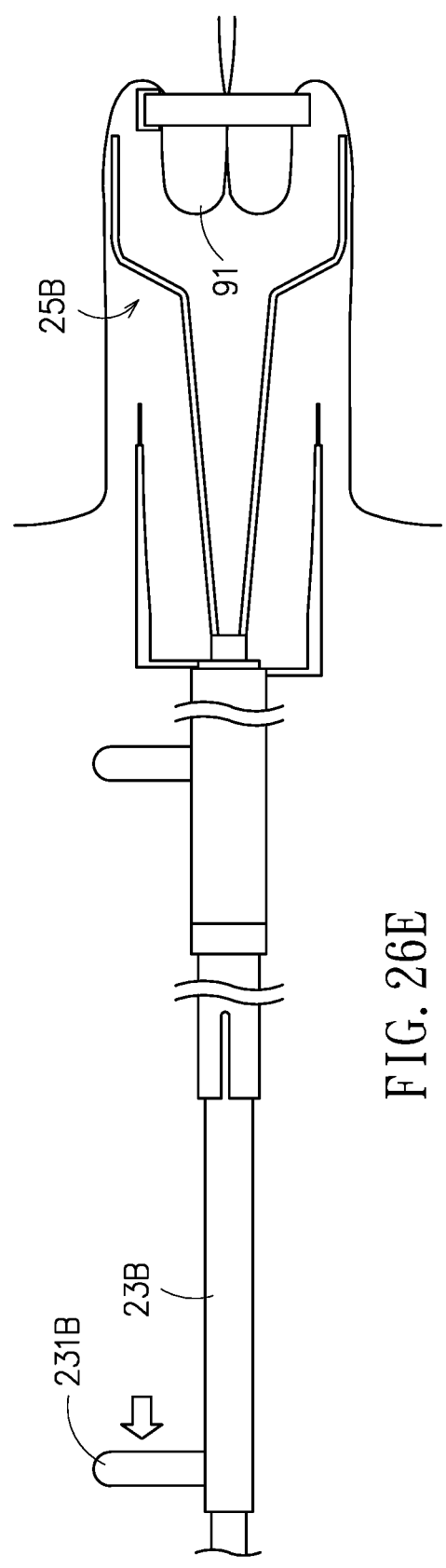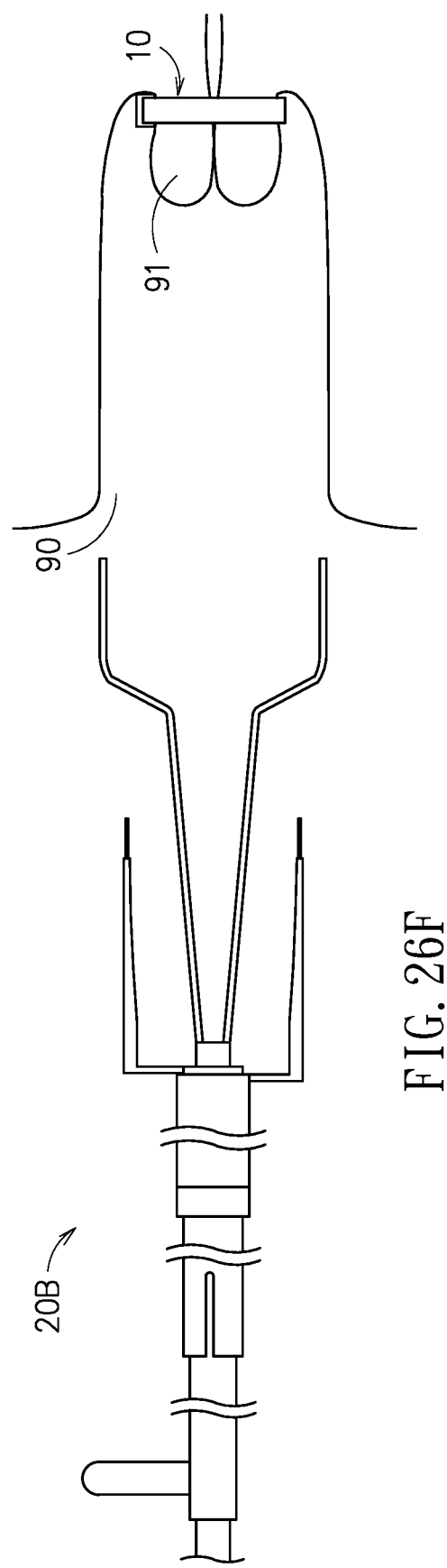

DEVICE, INSTRUMENT AND BELT FOR TYING CERVIX

CROSS REFERENCE TO RELATED APPLICATIONS

This application claims the benefits of Taiwan applications Serial No. 106144244 filed on Dec. 15, 2017, and Serial No. 107142412 filed on Nov. 28, 2018, the disclosures of which are incorporated by references herein in its entirety.

TECHNICAL FIELD

The present disclosure relates in general to a device, instrument and belt for tying a cervix, and more particularly to the device, instrument and belt that can be simply structured and easily operated to tie a cervix.

BACKGROUND

In the art, preterm birth is defined as a delivery prior to a 37-week pregnancy. Currently, in the maternal-fetal medicine, at least two kinds of pregnant women would be entitled in the high risk group of preterm birth. One is a pregnant woman who has a preterm birth history. Another is a pregnant woman whose cervix length is less than 25 mm. To this kind of pregnant women, even though no significant evidence of preterm birth is shown, the possibility thereof is still high. In the medical art, a cervix length measurement is usually introduced to screen specific pregnant women in the risk group of preterm birth. Nevertheless, regarding the aforesaid two kinds of pregnant women in the high risk of preterm birth, especially to those who are patients of cervical insufficiency, current policies against the preterm birth include at least the cervical cerclage and the pessary. The cervical cerclage uses sutures to completely stitch up the cervical orifice of the pregnant woman. On the other hand, the pessary is planted inside the vagina so as hopefully to stabilize the womb by fixing the cervix at a specific angle, such that the fetus can be prevented from descending, from which the cervical orifice would be forced to open earlier and eventually lead to a preterm birth.

Clinically, various evidences have proved that the cervical cerclage is effective to those pregnant women, whom are among the high risk group of preterm birth, and whom are patients of cervical insufficiency. However, to perform the cervical cerclage, the pregnant woman shall be anesthetized in advance, and this anesthetic process shall be performed by a qualified surgeon. In addition, since the majority of pregnant women usually concern the risk upon the fetus and the mother herself caused by the anesthetic process, related operations and even the hospitalization, thus the acceptability of the cervical cerclage does stay low. Beside the risk to the pregnant woman and the low acceptability, a braided suture among various sutures required in the surgery is usually concerned for having a minor rough woven surface, which won't be smoothened out after being tied. However, according to a British report, in a total number of about 700 pregnant women who accepted the cervical cerclage, 28% of the pregnant woman using the braided suture met the preterm birth, and 15% thereof met abortion or stillbirth; while 17% of the pregnant woman using the single-thread nylon suture met the preterm birth, and 5% thereof met abortion or stillbirth. It is highly doubt that one of possible causes accounted for fetus contamination is that the minor rough woven surface of the braided suture failed the sterilization of the operation.

On the other hand, regarding the pessary, recent clinical testing has proved that the usage of the pessary does not reduce the occurrence rate of preterm birth for single-fetus pregnancy.

Accordingly, if there is a device, instrument and belt for tying a cervix of a pregnant woman that can be immediately applied clinically without a surgery, an anesthetic process and even hospitalization, the acceptability thereof by pregnant women would be significantly increased, and the occurrence rate of the preterm birth would be substantially reduced. Thereupon, such an improvement is definitely urgent to the skill in the art.

SUMMARY

In one embodiment of this disclosure, a device for tying a cervix includes a belt and an instrument. The belt is used to tie a cervix. The instrument, applied to tie the belt onto the cervix, includes a first outer pipe, a second outer pipe and two fork structures. The second outer pipe is rotatable with respect to the first outer pipe. The two fork structures are connected individually to corresponding axial ends of the first outer pipe and the second outer pipe, respectively, and each of the two fork structures is to be detachably inserted into the belt.

In another embodiment of this disclosure, an instrument includes a first outer pipe, a second outer pipe and two fork structures. The second outer pipe is rotatable with respect to the first outer pipe. The two fork structures, connected individually to corresponding axial ends of the first outer pipe and the second outer pipe, respectively, are to be inserted into a belt detachably.

In a further embodiment of this disclosure, a belt includes a head portion, a middle portion and a tail portion. The head portion has a head-end plug hole and a head-end through hole. The head-end through hole is furnished thereinside with an inner teeth structure. The tail portion has a tail-end plug hole. The middle portion, located between the head portion and the tail portion, having at least one section thereof with two opposing lateral sides to provide individual outer teeth structures to pair the inner teeth structure, the head-end plug hole and the tail-end plug hole being inserted detachably by two fork structures of an instrument, respectively.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein:

FIG. 9A demonstrates schematically the pairing of the second handle and the positioning slot in the instrument of FIG. 7;

FIG. 9B is a schematic cross-sectional view of the sliding slots and the sliding node in the instrument of FIG. 7;

FIGS. 15A-15C are a top view, a front view and a left-side view of a belt of FIG. 1 in an extended state, respectively;

FIGS. 21A-21C are a top view, a front view and a left-side view of the belt in accordance with another embodiment of this disclosure, respectively;

FIGS. 22A-22C are a top view, a front view and a left-side view of the head portion of the belt of FIGS. 21A-21C, respectively;

FIG. 23 demonstrates schematically an engagement state between the middle portion and the head portion of the belt of FIGS. 21A-21C;

FIGS. 24A-24C are a top view, a front view and a left-side view of the belt in accordance with yet another embodiment of this disclosure, respectively;

FIGS. 25A-25F demonstrate different stages of operation of the embodiment of FIG. 1; and FIGS. 26A-26F demonstrate different stages of operation of the embodiment of FIG. 7.

DETAILED DESCRIPTION

Figure 1:
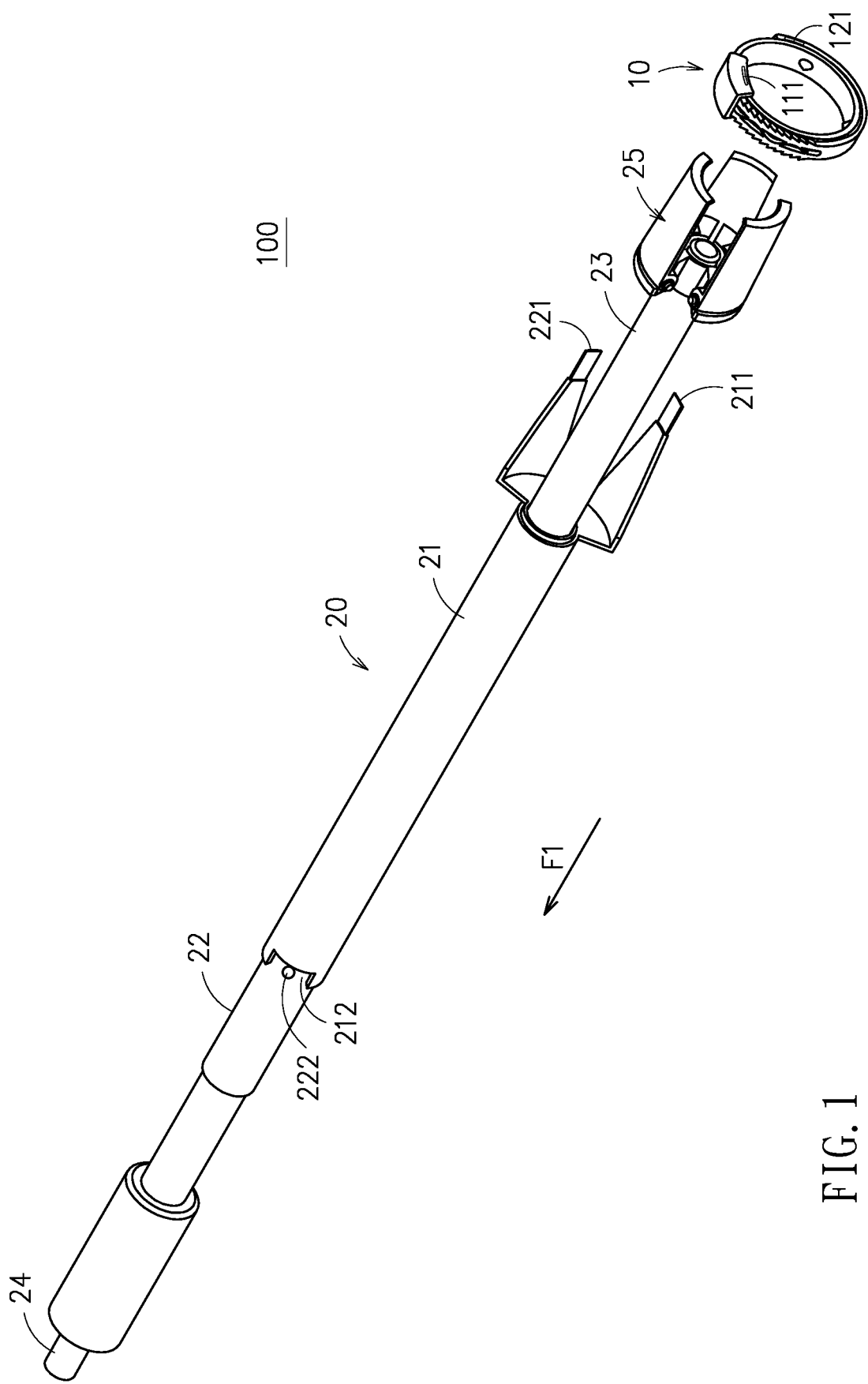
FIG. 1 is a schematic perspective view of a device for tying a cervix in accordance with an embodiment of this disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Referring now to the embodiment shown in FIG. 1, the device for tying a cervix 100 includes a belt 10 and an instrument 20. The belt 10 for tying the cervix is to forbid a cervical orifice to open. The instrument 20 is to apply and thus tie the belt 10 onto the cervix. The belt 10 can be made of a biocompatible elastic plastics, such that the belt 10 can be left inside a human body without making any specific damage.

Figure 2:
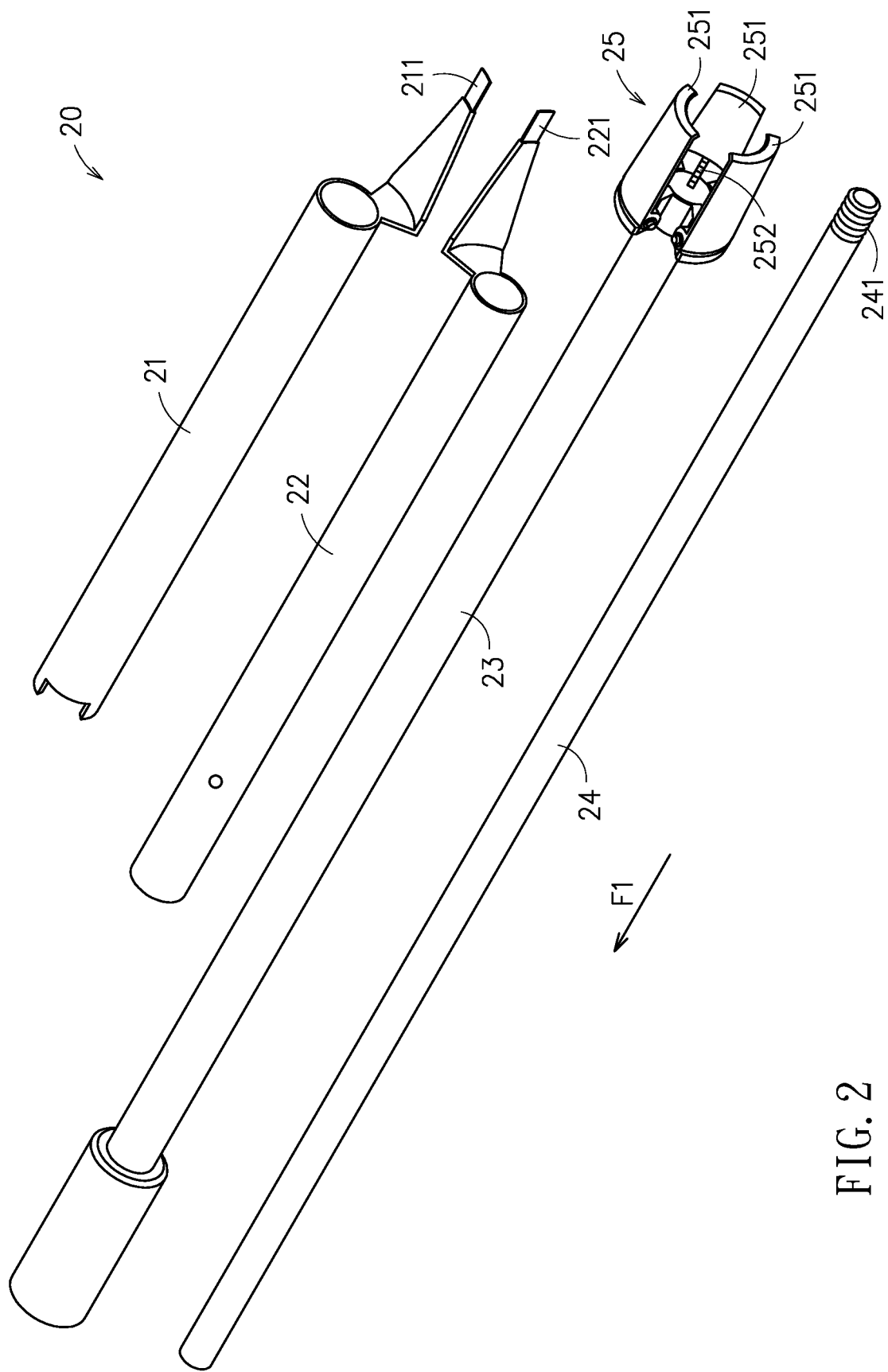
FIG. 2 is a schematic exploded view of an instrument of the device of FIG. 1.
Figure 3:
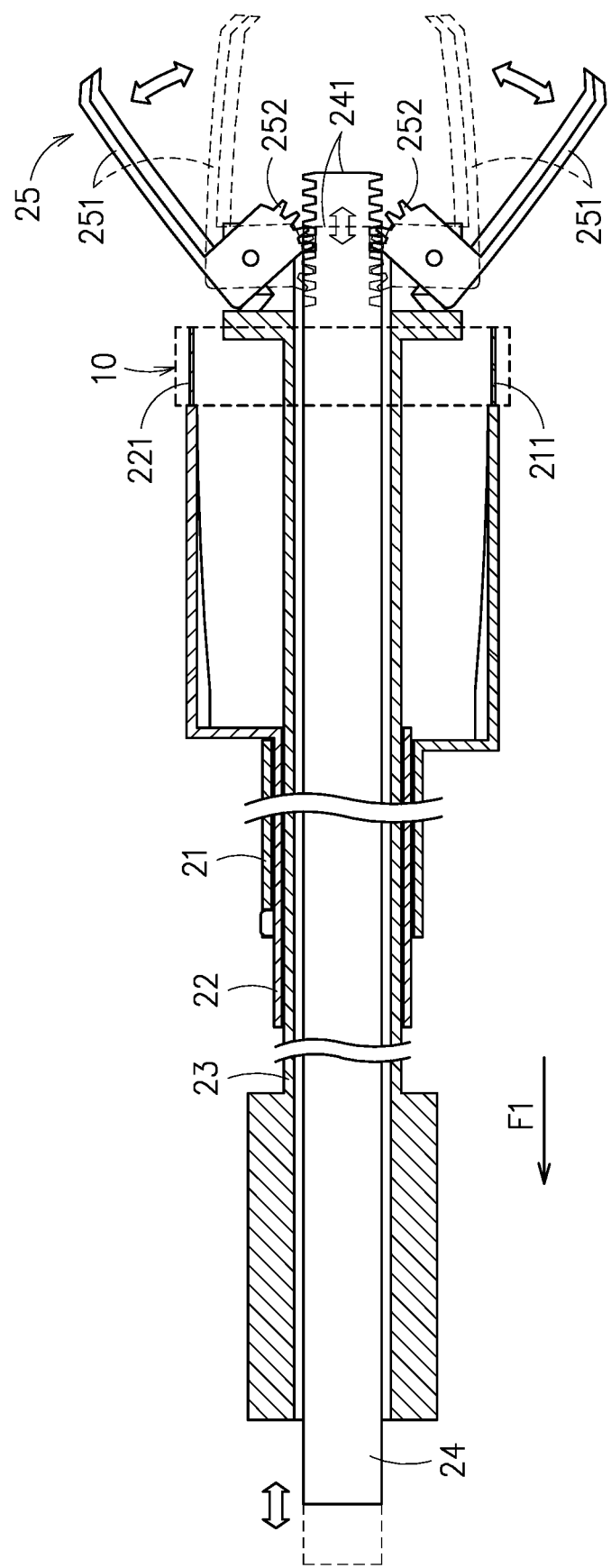
FIG. 3 is a schematic cross-sectional view showing different states of the instrument of FIG. 1.

Referring now to FIG. 1 through FIG. 3, the instrument 20 includes a first outer pipe 21, a second outer pipe 22, a first inner pipe 23 and a second inner pipe 24, in which the first outer pipe 21, the second outer pipe 22, the first inner pipe 23 and the second inner pipe 24 are all coaxial. In this embodiment, the first outer pipe 21, the second outer pipe 22, the first inner pipe 23 and the second inner pipe 24 are telescoped orderly inwards and rotational to each other. In particular, the first outer pipe 21 can rotate about the second outer pipe 22. Two fork structures 211, 221 are individually connected to corresponding axial ends of the first outer pipe 21 and the second outer pipe 22, respectively. Free ends of these two fork structures 211, 221 are together to handle the belt 10, through inserting in a detachable manner. An axial end of the first inner pipe 23 connects a claw mechanism 25. The claw mechanism 25 includes, but not limited to, three claw fingers 251. The second inner pipe 24, sleeved axially by the first inner pipe 23, can move with respect to the second inner pipe 24. Each inner diameter of the fork structures 211, 221 is greater than an outer diameter of the claw mechanism 25, such that the fork structures 211, 221 can move back and forth about the claw mechanism 25 in an axial direction F1.

Referring now to FIG. 3, in each of the claw fingers 251, a gear 252 is pivotally mounted to an inner side of a root of the claw finger 251, and a rack 241 to mesh the gear 252 is constructed axially and exteriorly at the axial end of the second inner pipe 24. Thereupon, the claw mechanism 25 can connect the second inner pipe 24 via meshing the gear 252 and the rack 24. As the second inner pipe 24 performs an axial moment with respect to the first inner pipe 23, the rack 241 would rotate the respective gears 252 simultaneously so as to open/close the three claw fingers 251.

Figure 4:
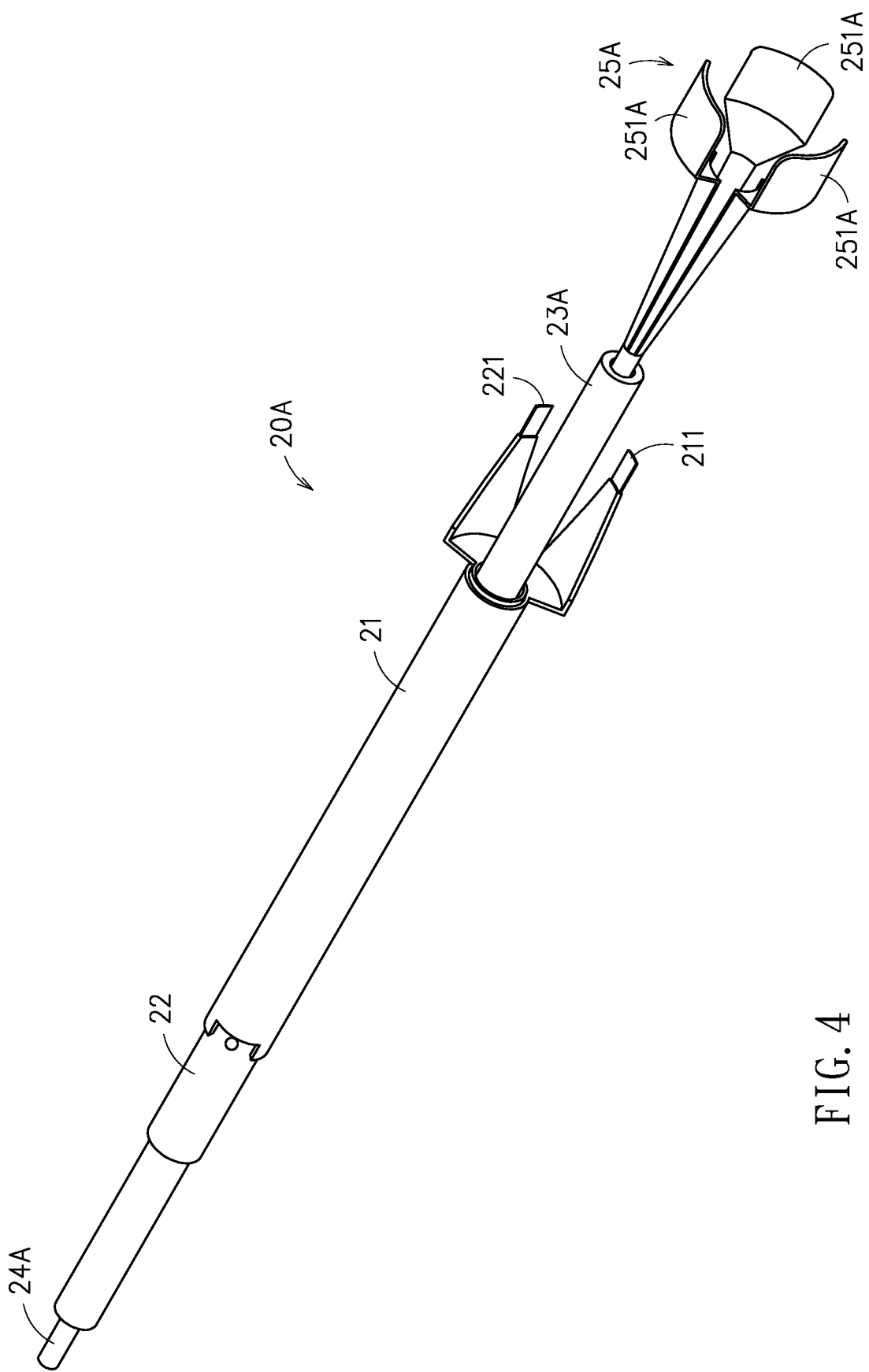
FIG. 4 is a schematic perspective view of the instrument for tying a cervix in accordance with another embodiment of this disclosure.
Figure 5:
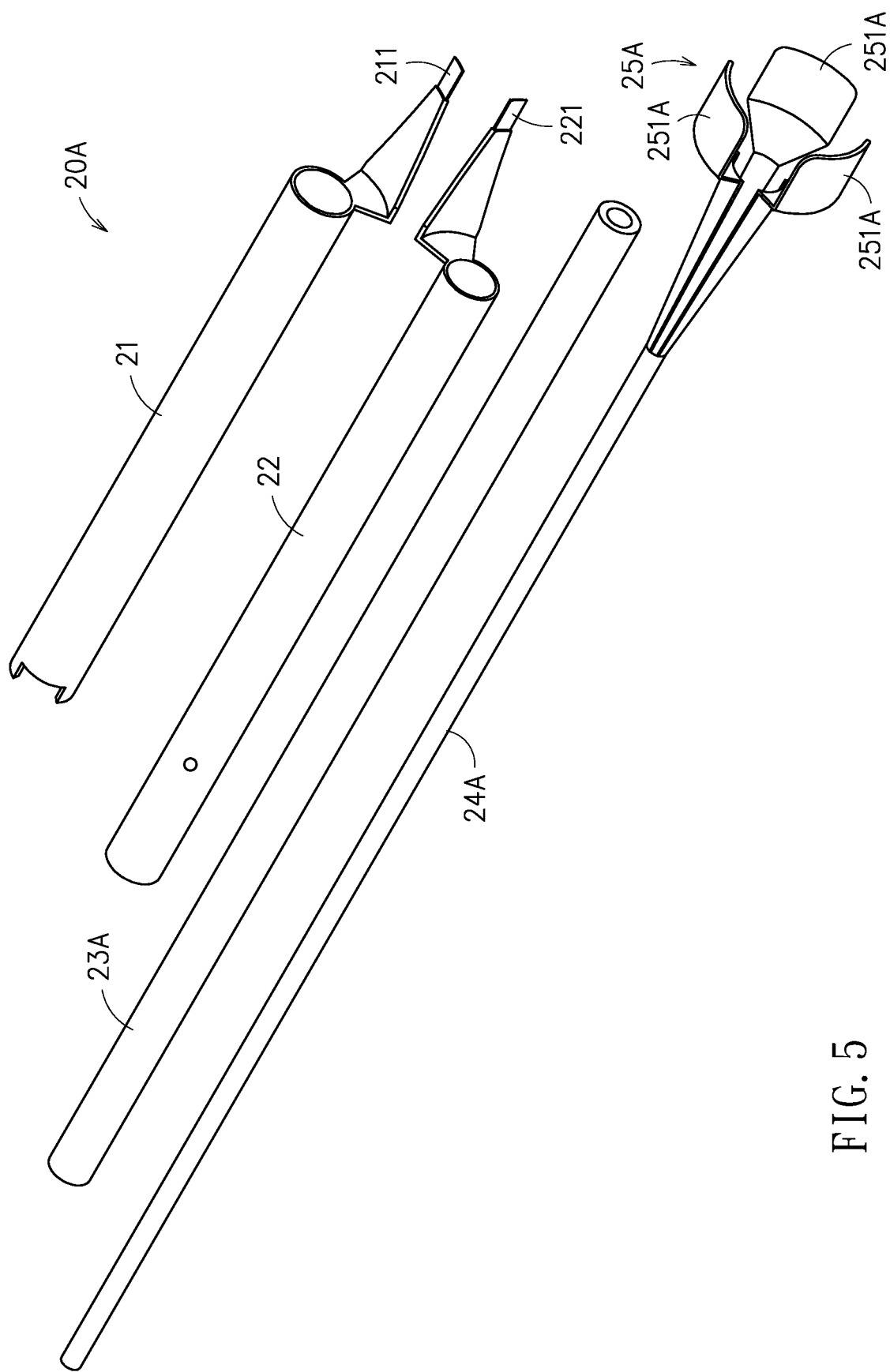
FIG. 5 is a schematic exploded view of FIG. 4.
Figure 6:
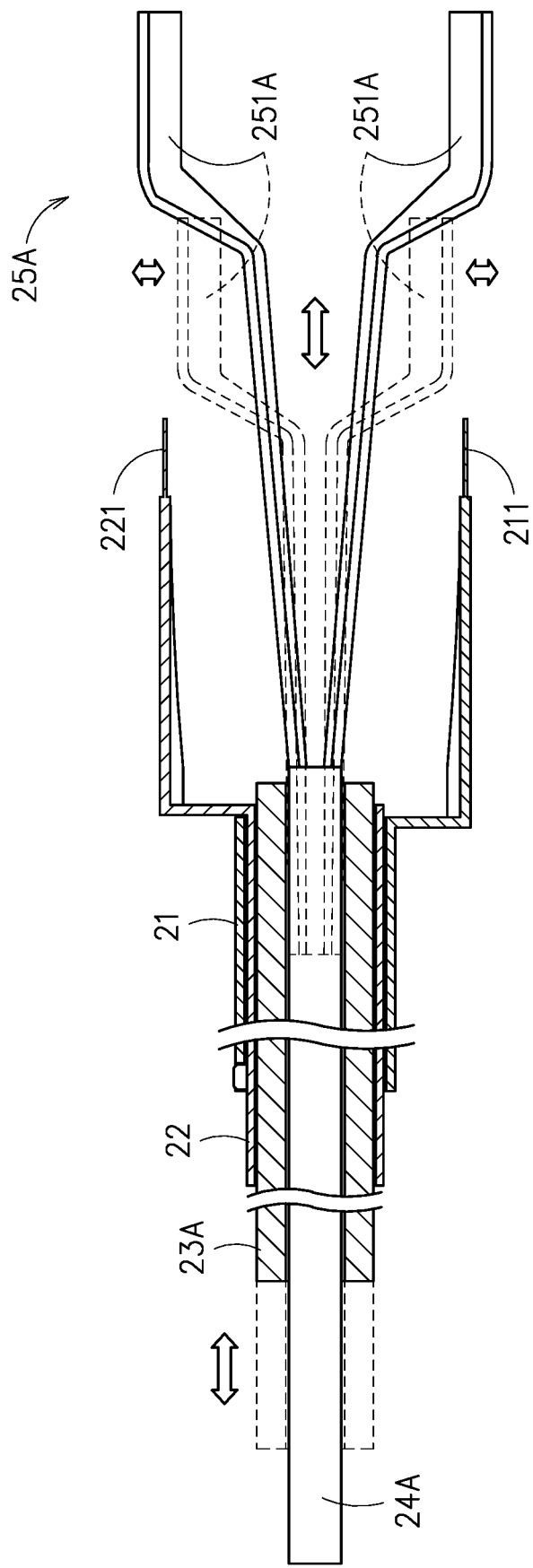
FIG. 6 is a schematic cross-sectional view showing different states of the instrument of FIG. 4.

Referring now to FIG. 4 through FIG. 6, another embodiment of the instrument according to this disclosure is shown. This instrument 20A includes a first outer pipe 21, a second outer pipe 22, a first inner pipe 23A and a second inner pipe 24A. Two fork structures 211, 221 are individually connected to corresponding axial ends of the first outer pipe 21 and the second outer pipe 22, respectively. Free ends of these two fork structures 211, 221 are together to handle the belt 10 of FIG. 1, through inserting in a detachable manner. In this embodiment, an axial end of the second inner pipe 24A connects a claw mechanism 25A. The claw mechanism 25A includes, but not limited to, three cantilever structures 251A extending outwards individually from the second inner pipe 24A. Each of the cantilever structures 251A is connected to the axial end of the second inner pipe 24A via a connecting member 252A, and the connecting member 252A is extended outward radially from the axial end of the second inner pipe 24A, such that the claw mechanism 25A can present an axial diffusion state. The second inner pipe 24A, axially mounted inside the first inner pipe 23A, can move axially along the first inner pipe 23A.

Referring now to FIG. 6, when the claw mechanism 25A protrudes out from the first inner pipe 23A, the three cantilever structures 251A, pre-stressed together to be stored axially into the first inner pipe 23A, would expand radially outwards. On the other hand, when the three cantilever structures 251A are retrieved into the first inner pipe 23A, the three cantilever structures 251A would be forced to form a bundle in the first inner pipe 23A. Namely, as the second inner pipe 24A slides axially with respect to the first inner pipe 23, the claw mechanism 25A would perform open or close accordingly via expanding or bundling these three cantilever structures 251A.

Figure 7:
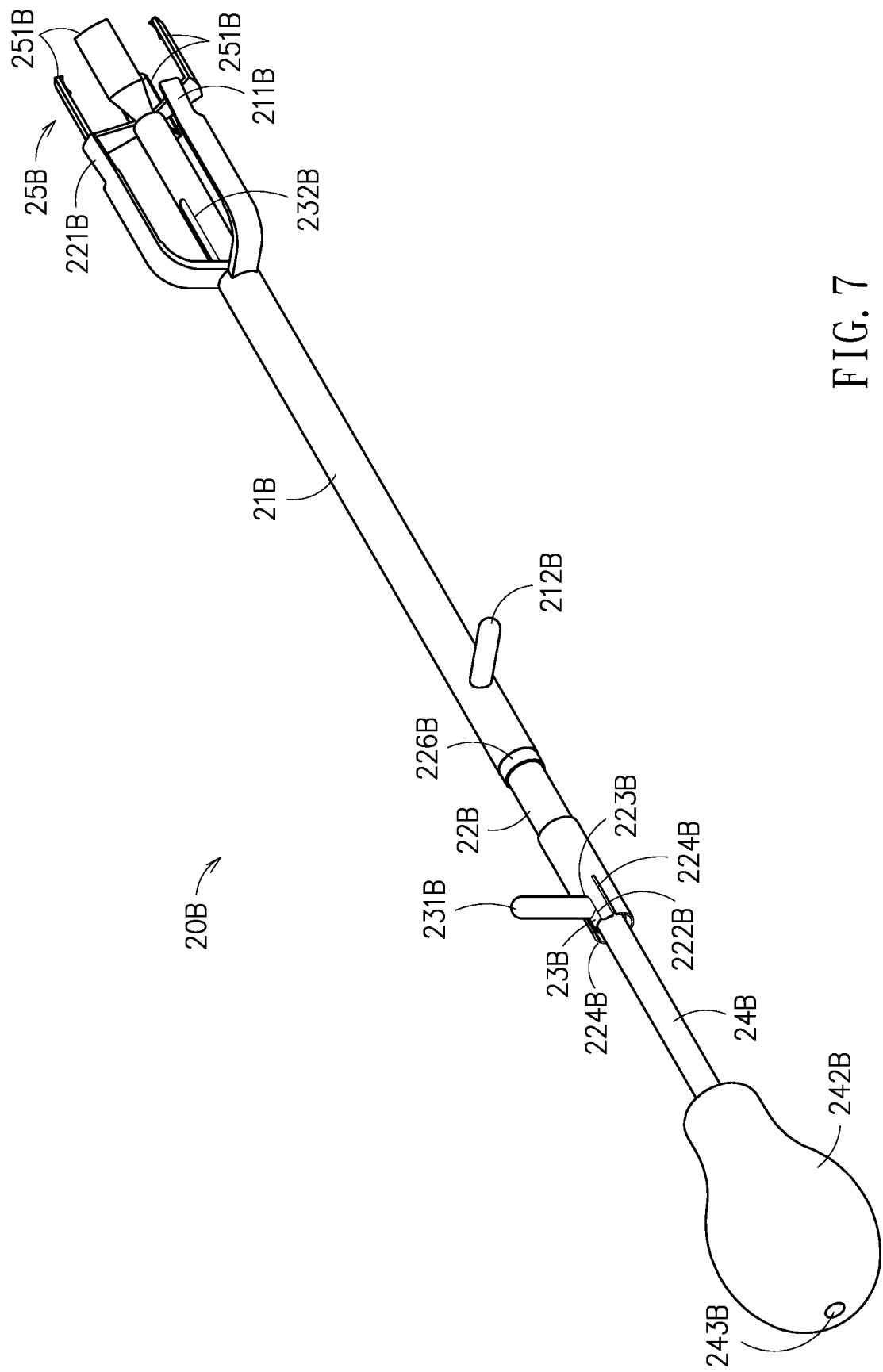
FIG. 7 is a schematic perspective view of the instrument for tying a cervix in accordance with a further embodiment of this disclosure.
Figure 8:
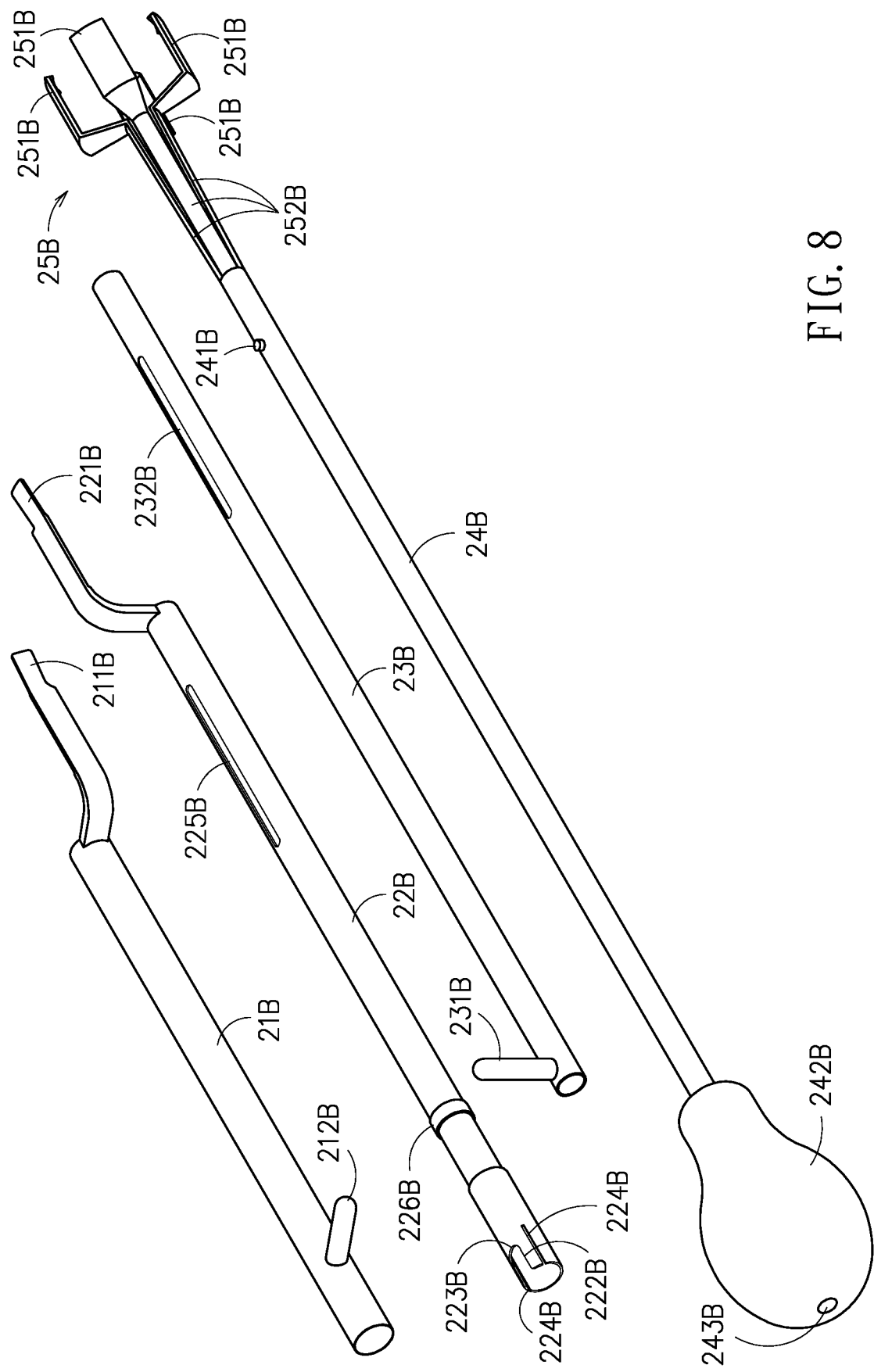
FIG. 8 is a schematic exploded view of FIG. 7.

Referring now to FIG. 7 and FIG. 8, in this embodiment, the instrument 20B includes a first outer pipe 21B, a second outer pipe 22B, a first inner pipe 23B and a second inner pipe 24B. The two fork structures 211B, 221B are individually connected to corresponding axial ends of the first outer pipe 21B and the second outer pipe 22B, respectively. The fork structures 211B, 221B can plug into the belt 20 of FIG. 1 in a detachable manner. An axial end of the second inner pipe 24B is connected with a claw mechanism 25B. The claw mechanism 25B includes four cantilever structures 251B extended outward from the second inner pipe 24B, each of the cantilever structures 251B is connected to the axial end of the second inner pipe 24B via a connecting member 252B, and the connecting member 252B is extended outward radially from the axial end of the second inner pipe 24B, such that the claw mechanism 25B can present an axial diffusion state. In this disclosure, it shall be understood that the number of the cantilever structures 251B is not strictly limited to be four. The second inner pipe 24B, axially mounted inside the first inner pipe 23B, can move axially along the first inner pipe 23B.

It can be seen that the embodiment shown in FIGS. 7-8 is basically an improvement of that shown in FIGS. 4-6. In particularly, this embodiment of FIGS. 7-8 is further furnished with mechanisms for limiting relative movements among pipes and some other auxiliary structures, so as thereby to enable a simpler operation.

Referring now to FIG. 7 and FIG. 8, the first outer pipe 21B is furnished with a first handle 212B, and a step ring 226B is constructed fixedly to an outer surface of the second outer pipe 22B. Thereupon, the first outer pipe 21B is mounted between the step ring 226B and the fork structure 221B of the second outer pipe 22B, such that the axial movement of the first outer pipe 21B can be limited but the rotational movement thereof is allowed.

Referring now to FIG. 7 through FIG. 9A, the second outer pipe 22B has a positioning slot 222B located at another axial end thereof opposite to the axial end having the fork structure 221B. The positioning slot 222B extends axially along the second outer pipe 22B by a predetermined length to connect spatially a round hole 223B. The second outer pipe 22B further has a pair of axial slits 224B to sandwich the positioning slot 222B lengthwise. In addition, the first inner pipe 23B is furnished with a second handle 231B.

Referring to FIG. 9A, a width of the positioning slot 222B is less than an outer diameter of the second handle 231B, and a diameter of the round hole 223B is equal to or larger than the outer diameter of the second handle 231B. With the first inner pipe 23B to be telescoped inside the second outer pipe 22B, while the second handle 231B is moved axially to enter the positioning slot 222B, the positioning slot 222B would be enlarged to accommodate the second handle 231B due to the arrangement of the pairing slits 224B, and thus the second handle 231B can move all the way along the positioning slot 222B to the round hole 223B. After the second handle 231B reaches the round hole 223B, the positioning slot 222B would resume its original dimensions to restrict the second handle 231B in the round hole 223B.

Referring to FIG. 8 and FIG. 9B, the second outer pipe 22B is furnished with a second-outer-pipe sliding slot 225B to extend axially along the second outer pipe 22B by a predetermined length, the first inner pipe 23B is furnished with a first-inner-pipe sliding slot 232B to extend axially along the first inner pipe 23B by another predetermined length, and the second inner pipe 24B is furnished with a sliding node 241B.

By telescoping orderly the first outer pipe 21B, the second outer pipe 22B, the first inner pipe 23B, and the second inner pipe 24B, the second-outer-pipe sliding slot 225B would be located at a position in correspondence with the first-inner-pipe sliding slot 232B, with the sliding node 241B to be restrained inside both the second-outer-pipe sliding slot 225B and the first-inner-pipe sliding slot 232B. In particular, a top of the sliding node 241B would not contact an inner wall of the first outer pipe 21B, so that, while the second inner pipe 24B undergoes an axial movement, the sliding node 241B can slide smoothly along both the second-outer-pipe sliding slot 225B and the first-inner-pipe sliding slot 232B, without being interfered by the inner wall of the first outer pipe 21B. Namely, the top of the sliding node 241B and the inner wall of the first outer pipe 21B are paired in a non-interference manner. In addition, an outer diameter of the sliding node 241B is less than both a width of the second-outer-pipe sliding slot 225B and that of the first-inner-pipe sliding slot 232B, such that the sliding node 241B can slide smoothly along both the second-outer-pipe sliding slot 225B and the first-inner-pipe sliding slot 232B without any interference. Upon the arrangement of the sliding node 241B, the second-outer-pipe sliding slot 225B and the first-inner-pipe sliding slot 232B, relative rotations among the second outer pipe 22B, the first inner pipe 23B and the second inner pipe 24B are prohibited.

Figure 10:
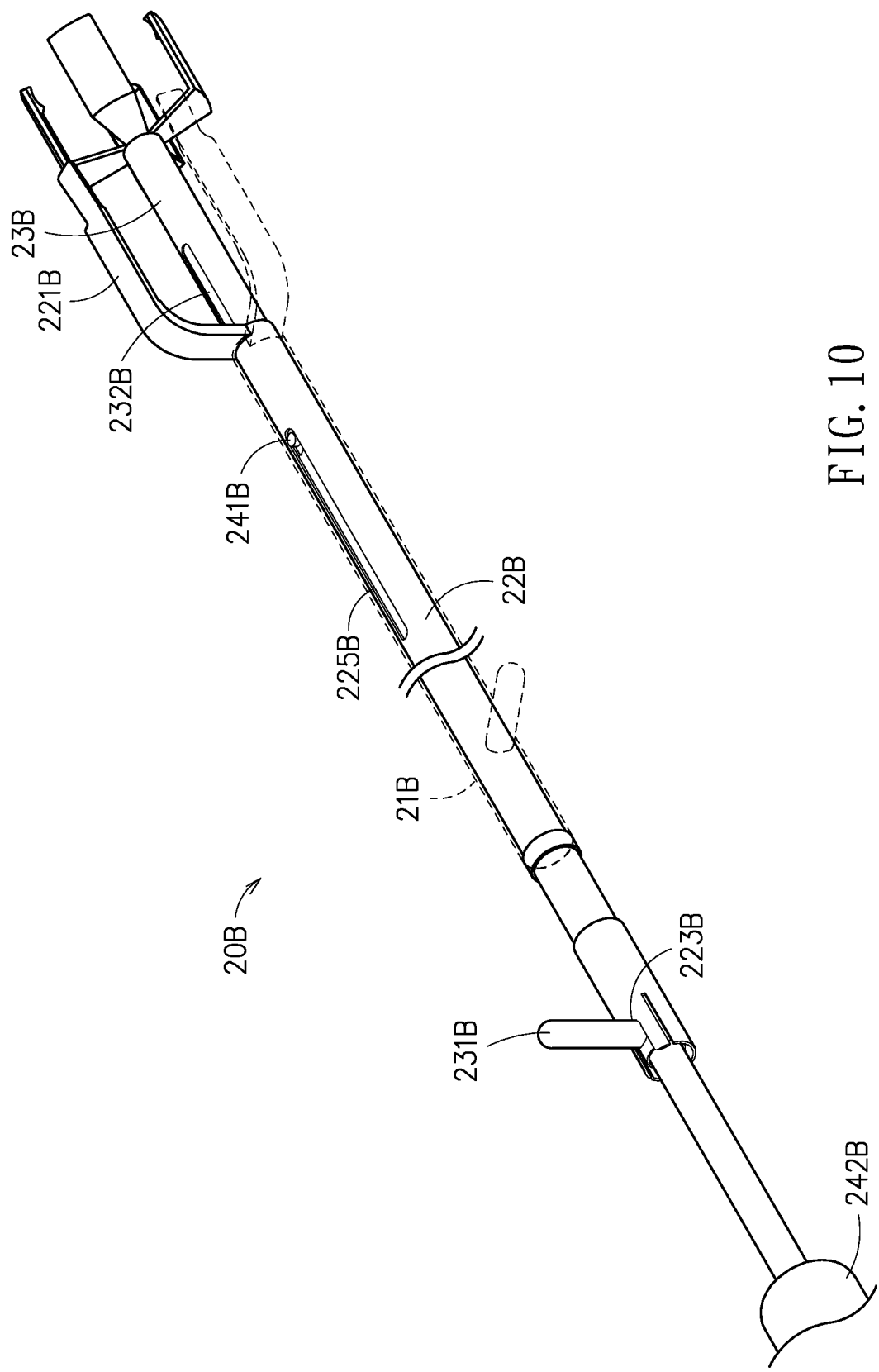
FIGS. 10-12 demonstrate schematically different states of the instrument of FIG. 7, showing particularly relative positions of the sliding slots and the sliding node.
Figure 11:
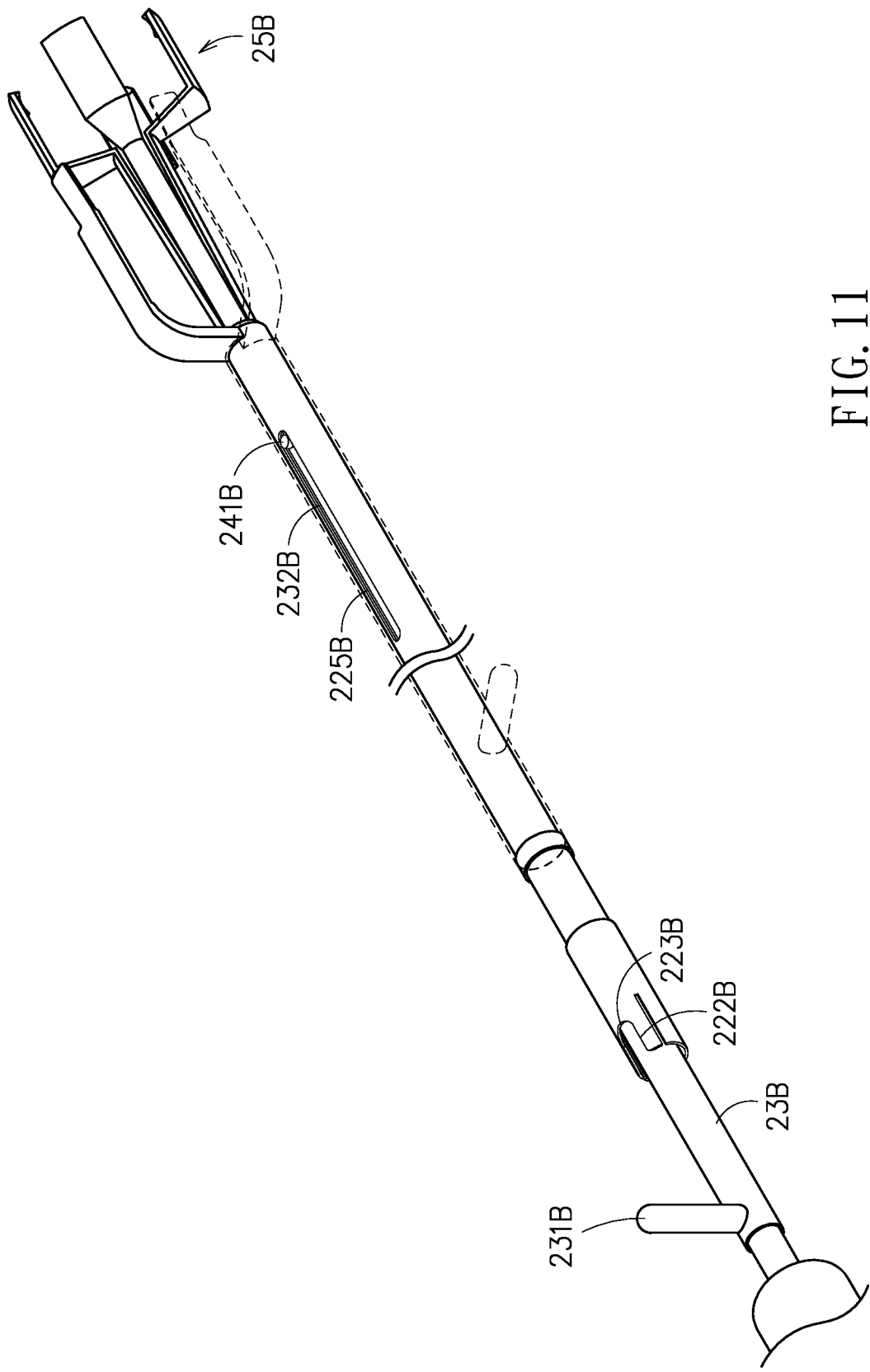
Figure 12:
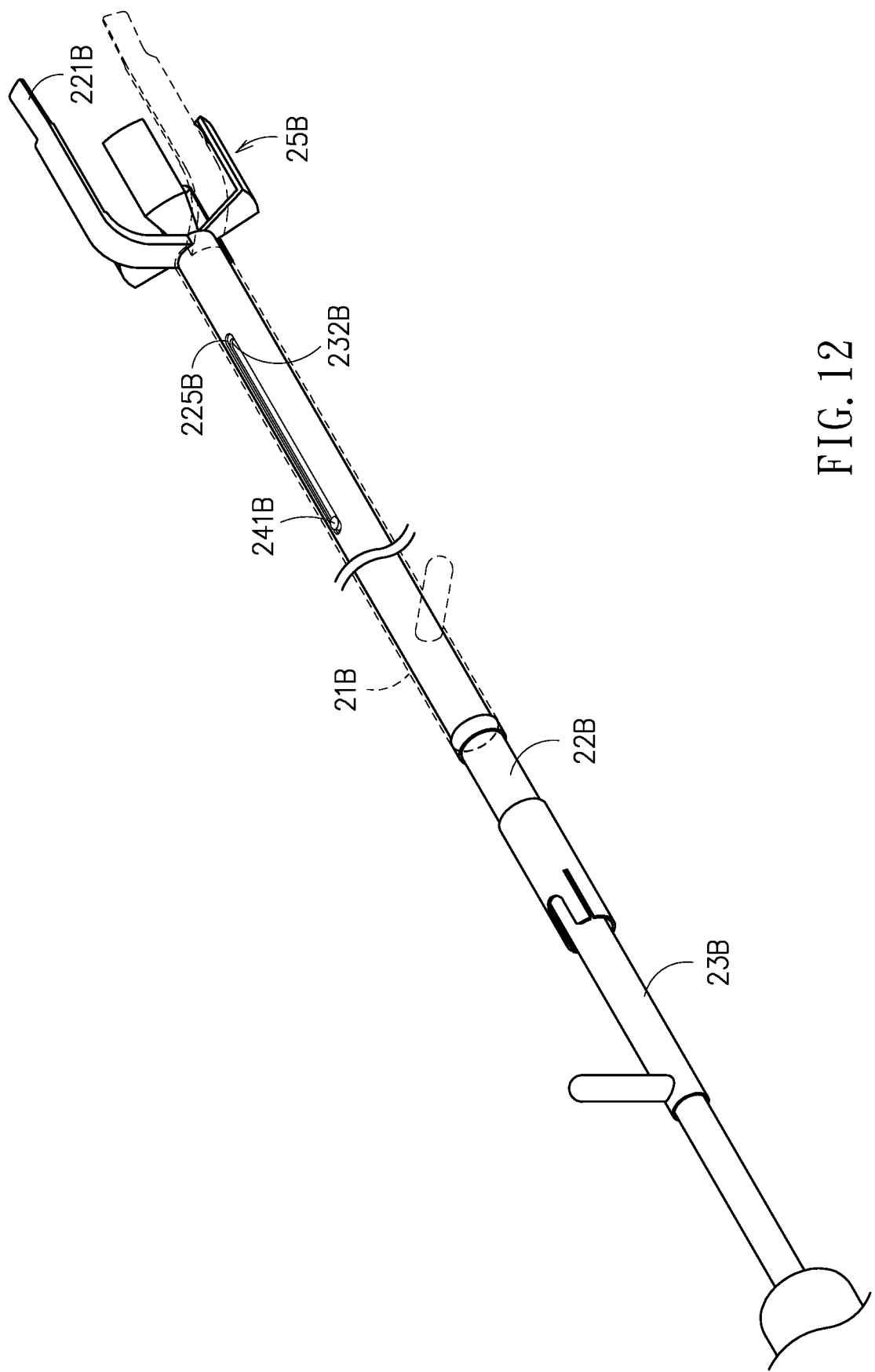

Referring now to FIG. 10 through FIG. 12, relative positioning of the second-outer-pipe sliding slot 225B, the first-inner-pipe sliding slot 232B and the sliding node 241B in different states of the instrument 20B are demonstrated.

As shown in FIG. 10, the first inner pipe 23B is pushed to stop axially toward the claw mechanism 25B till the claw mechanism 25B reaches a close state. At the same time, the first outer pipe 21B and the second outer pipe 22B are moved simultaneously toward the end having a grip 242B, so that the second handle 231B can be buckled inside the round hole 223B, the sliding node 241B can reach an end of the second-outer-pipe sliding slot 225B adjacent to the fork structure 221B, and also the sliding node 241B can reach an end of the first-inner-pipe sliding slot 232B adjacent to the second handle 231B.

As shown in FIG. 11, the first inner pipe 23B is pulled away from the claw mechanism 25B, so that, as the second handle 231B has been retrieved from the positioning slot 222B and the round hole 223B, the sliding node 241B reaches the end of the second-outer-pipe sliding slot 225B adjacent to the fork structure 221B, and also the sliding node 241B reaches an end of the first-inner-pipe sliding slot 232B away from the second handle 231B.

As shown in FIG. 12, the first inner pipe 23B is pushed to stop toward the claw mechanism 25B, and then the first outer pipe 21B and second outer pipe 22B are both pushed to stop toward the claw mechanism 25B as well, such that the sliding node 241B reaches an end of the second-outer-pipe sliding slot 225B away from the fork structures 221B, and also the sliding node 241B reaches the end of the first-inner-pipe sliding slot 232B adjacent to the second handle 231B.

Figure 13:
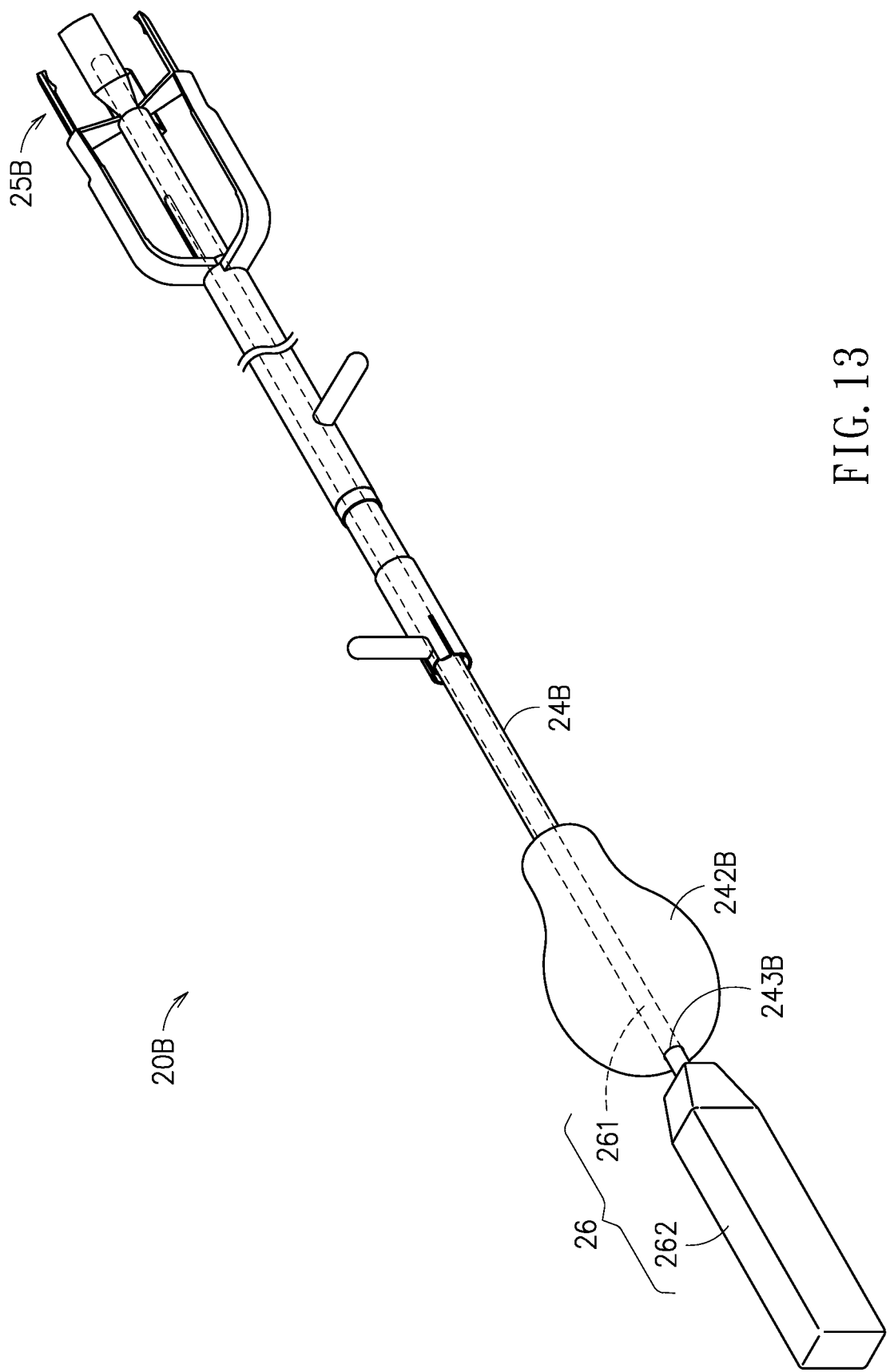
FIG. 13 is a schematic view showing the instrument of FIG. 7 and a paired lighting device.

Referring now to FIG. 7, FIG. 8 and FIG. 13, a hand grip 242B is furnished to another axial end of the second inner pipe 24B away from the claw mechanism 25B. The hand grip 242B convenient for an user to operate the instrument 20B has a central through hole 243B axially establishing a spatial connection between the interior of the second inner pipe 24B and that of hand grip 242B. A lighting device 26, able to be plugged into an free end of the central through hole 243B away from the second inner pipe 24B, can provide illumination to the axial end of the second inner pipe 24B adjacent to the claw mechanism 25B. The lighting device 26 is not limited to any specific type or configuration. For example, the lighting device 26 can be an elongated light source 261 detachably connected with a control box 262. The control box 262 is to energize and control the light source 261. The light source 261 can be ready to use and disposable for one-time usage, while the control box 262 can be reused. In addition, the light source 261 can be an optical fiber or a light-guide rod. The hand grip 242B, the central through hole 243B and the lighting device 26 herein can be also applied to the instruments 20, 20A of FIG. 1 and FIG. 4, respectively. In the situation without the hand grip 242B and the central through hole 243B, the lighting device 26 can be plugged into the axial end of the second inner pipe 24B away from the claw mechanism 25B. In other words, while being applied to any of the instruments 20, 20A of FIG. 1 and FIG. 4, the lighting device 26 can be plugged from the axial end of the second inner pipe 24 or 24A away from the claw mechanism 25 or 25A, respectively. Preferably, while being plugged into the second inner pipe from the axial end of the second inner pipe away from the claw mechanism, the lighting device 26 can reach another axial end of the second inner pipe adjacent to the claw mechanism.

Figure 14A:
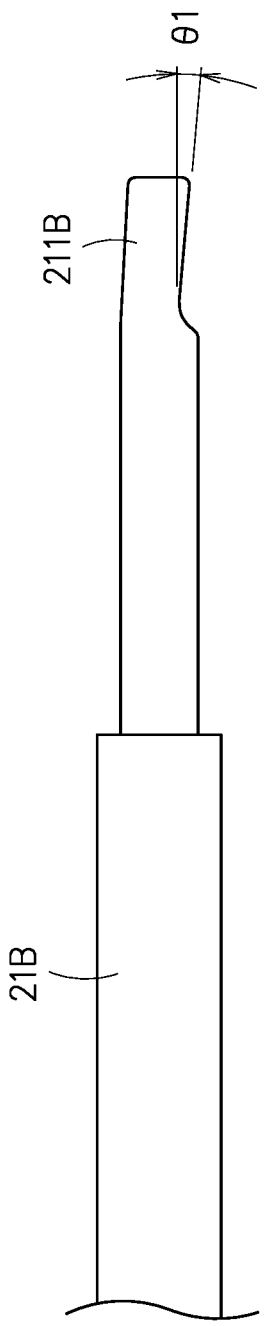
FIGS. 14A-14B demonstrate angling of the two fork structures in the instrument of FIG. 7.
Figure 14B:
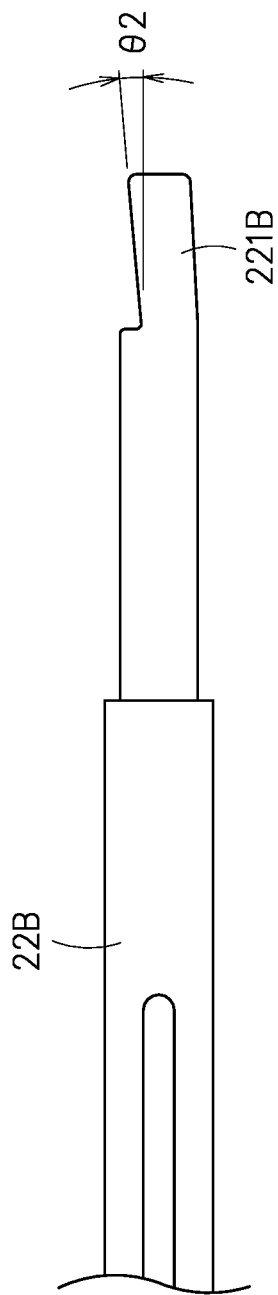

Referring now to FIGS. 14A and 14B, a first angle θ1 is formed by a lateral edge of the fork structure 211B of the first outer pipe 21B with respect to the axial direction of the first outer pipe 21B, and a second angle θ2 is formed by a lateral edge of the fork structure 221B of the second outer pipe 22B with respect to the axial direction of the second outer pipe 22B. As shown, the first angle θ1 and the second angle θ2 are leaned to different sides of the axial direction, and each of the first angle θ1 and the second angle θ2 is within a range of 1-45 degrees. Details about the fork structures 211B, 221B having oblique edges would be elucidated as follows.

Though different structuring of the claw mechanisms 25, 25A, 25B are shown in FIGS. 1-3, FIGS. 4-6 and FIGS. 7-8, respectively, yet the performances thereof are the same, all of which are achieved by sliding axially the first inner pipes 23, 23A, 23B with respect to the second inner pipes 24, 24A, 24B, respectively. Except for the pair of the gear 252 and the rack 241 in FIG. 3, in some other embodiments, a cam pair having an eccentric cam and a push rod or the like mechanism can also be applied to control the open/close of the claw mechanism.

Figure 17:
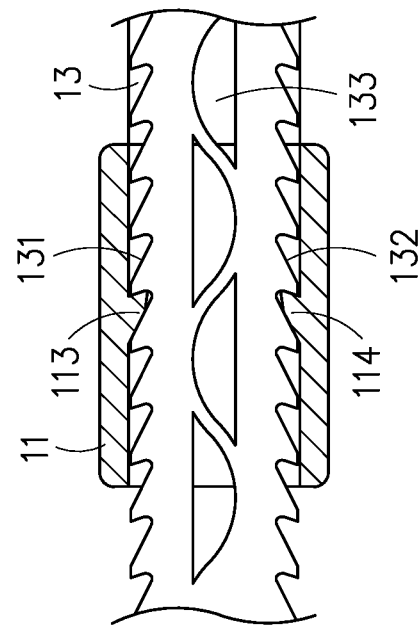
FIG. 17 demonstrates schematically an engagement state between a middle portion and the head portion of the belt of FIG. 1.
Figure 16A:
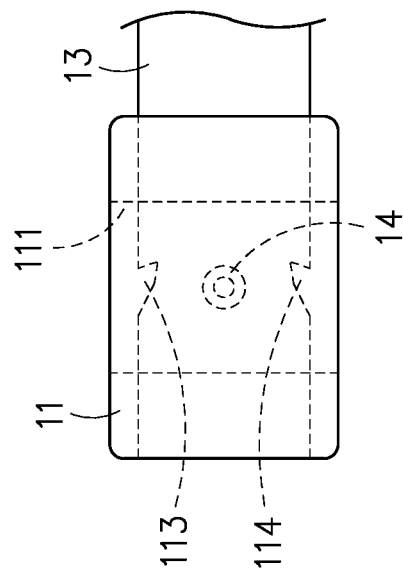
FIGS. 16A-16C are a top view, a front view and a left-side view of a head portion of the belt of FIG. 1, respectively.
Figure 16B:
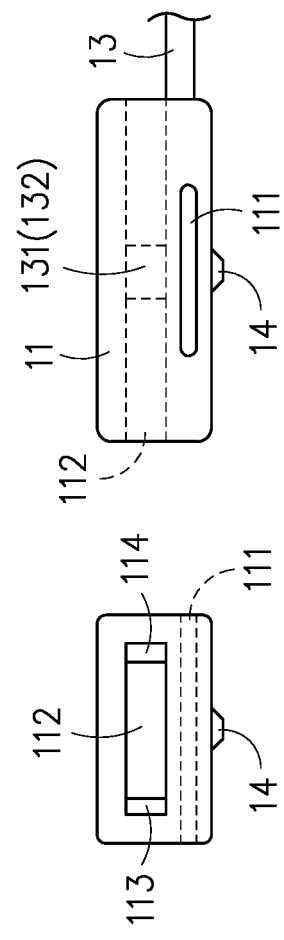
Figure 16C:
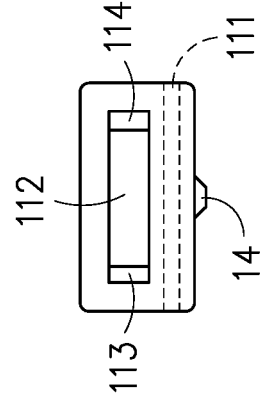

Referring now to FIGS. 15A-15C, FIGS. 16A-16C, FIG. 17 and FIG. 18, the belt 10 includes a head portion 11, a tail portion 12 and a middle portion 13. The head portion 11 has a head-end plug hole 111 and a head-end through hole 112. The head-end through hole 112 has an inner teeth structures 113, 114. The tail portion 12 has a tail-end plug hole 121. The middle portion 13, located between the head portion 11 and the tail portion 12, has at least one section with two opposing lateral sides to provide individual outer teeth structures 131, 132 to pair the inner teeth structures 113, 114, respectively. As shown in FIG. 15A, an elastic structure 133 is constructed at the belt 10 at a place between the two outer teeth structures 131, 132 of the middle portion 13. In this embodiment, the elastic structure 133 is a hollowed-out section in the middle portion 13 between the two outer teeth structures 131, 132 to provide a compressible room while the two outer teeth structures 131, 132 are compressed inwards. Upon such an arrangement, the resistance against pulling the middle portion 13 through the head portion 11 (i.e., in a tying direction of the belt 10) would be substantially reduced. In addition, the belt 10 further includes a plurality of bumps 14 on a surface thereof between the head portion 11 and the middle portion 13. In this embodiment, one of the bumps 14 is disposed on, but not limited to, the head portion 11. While in tying the belt 10, the tail portion 12 is sent to pierce the head-end through hole 112 of the head portion 11, with both the outer teeth structures 131, 132 of the middle portion 13 to engage the corresponding inner teeth structures 113, 114, as shown in FIG. 17. Thereby, the belt 10 can be in a state of an adjustable ring shown in FIG. 18, with the plurality of bumps 14 disposed at an inner side of the adjustable ring.

Figure 18:
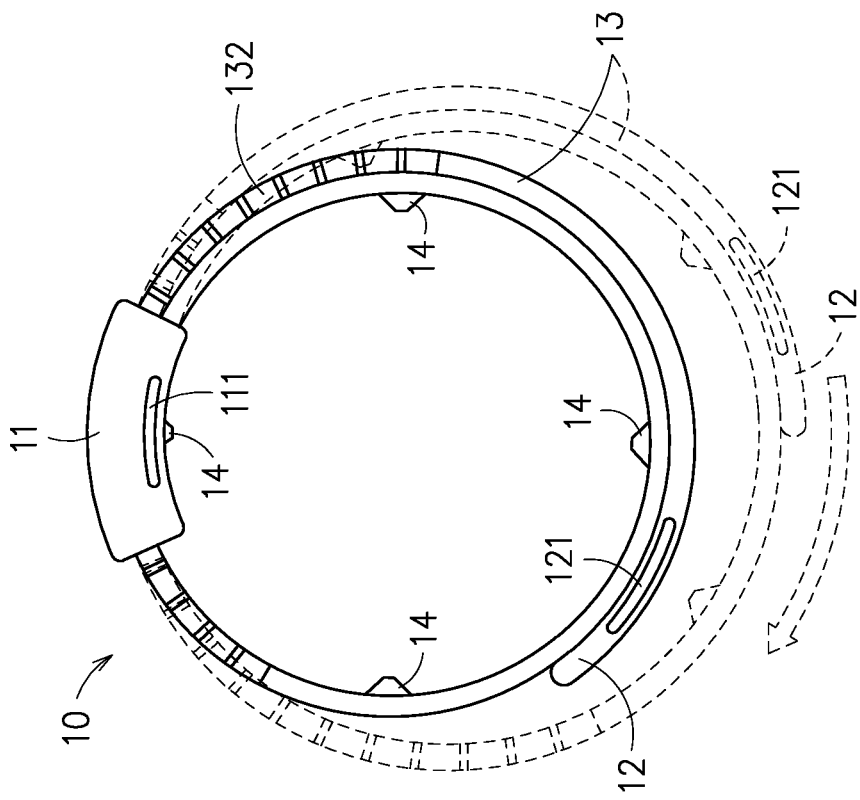
FIG. 18 demonstrates schematically an adjusted state of the belt of FIG. 1.
Figure 20:
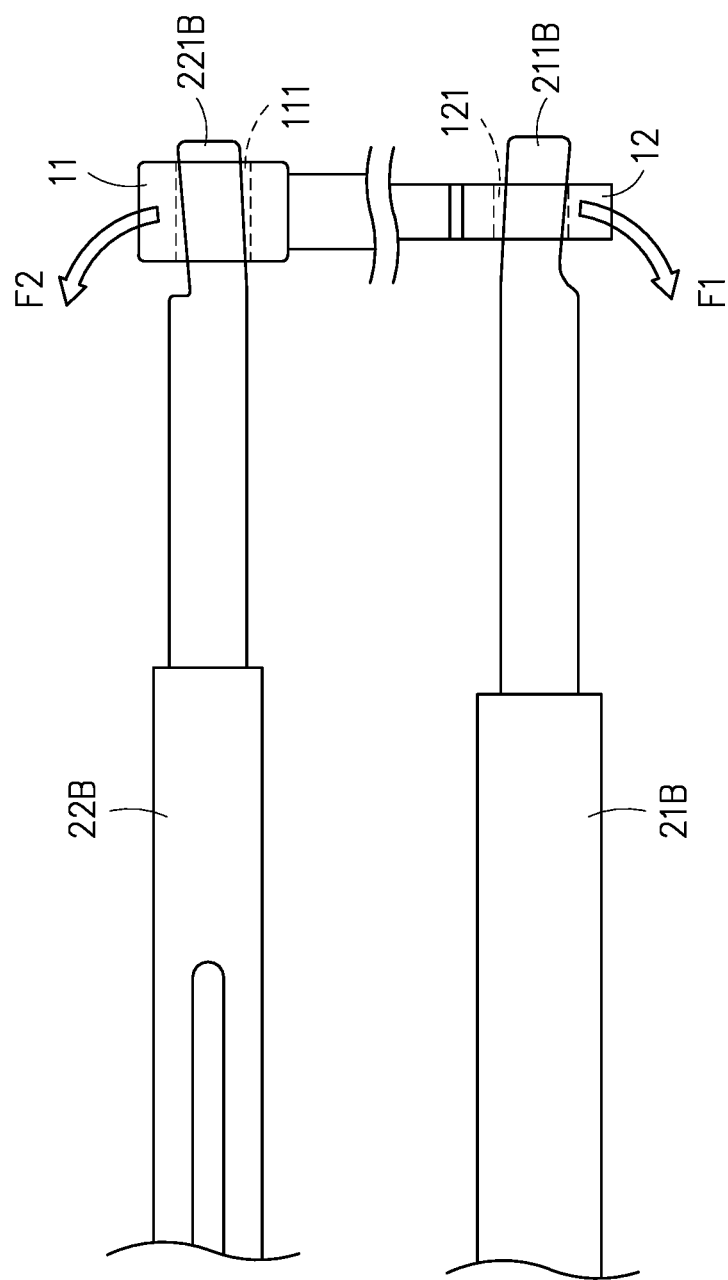
FIG. 20 demonstrates forcing of the two fork structures in the instrument of FIG. 7 upon the belt.

Referring now to FIG. 1 and FIG. 18, the two fork structures 211, 221 of the instrument 20 are sent to pierce the tail-end plug hole 121 and the head-end plug hole 111 of the belt 10, respectively. Then, with the second outer pipe 22 stationary, turn the first outer pipe 21 so as to have the fork structure 211 to move the tail portion 12 in a direction to shrink the inner diameter of the belt 10. In this step, an operator, a surgeon for example, can hold the second outer pipe 22 at one hand, and use another hand to rotate the first outer pipe 21, such that the tail portion 12 can be driven to decrease the inner diameter of the belt 10. Similarly, as shown in FIG. 4 through FIG. 6, the aforesaid manipulation can be applied for the instrument 20A to reduce the inner diameter of the belt 10.

Figure 19:
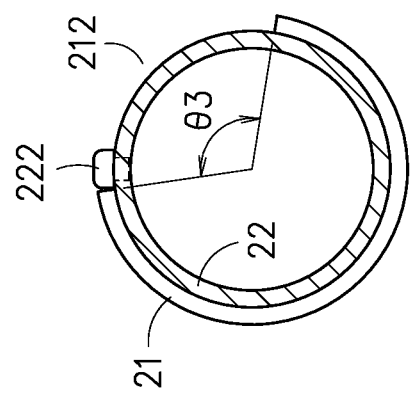
FIG. 19 is a schematic view showing related rotations between a first outer pipe and a the second outer pipe.

In addition, referring now to FIG. 1 and FIG. 19, at least one constraint structure can be constructed to the first outer pipe 21 and the second outer pipe 22 so as to limit the relative rotatable angle between the first outer pipe 21 and the second outer pipe 22. For example, a stop node 222 can be constructed at the second outer pipe 22, while a slot 212 corresponding to the stop node 222 is produced at the first outer pipe 21. Thereupon, the rotation angle θ3 of the first outer pipe 21 can be limited. However, it shall be understood that the magnitude of the rotation angle θ3 depends on practical needs, which can be any angle less than 360 degrees.

Referring now to FIG. 7, FIG. 14A, FIG. 14B, FIG. 18 and FIG. 20, the two fork structures 211B, 221B of the first outer pipe 21B and the second outer pipe 22B of the instrument 20 in FIG. 7 are sent to pierce the tail-end plug hole 121 and the head-end plug hole 111 of the belt 10, respectively. Then, with the second outer pipe 22B stationary, turn the first outer pipe 21B. Since the first angle θ1 is formed by the lateral edge of the fork structure 211B of the first outer pipe 21B with respect to the axial direction of the first outer pipe 21B, the second angle θ2 is formed by the lateral edge of the fork structure 221B of the second outer pipe 22B with respect to the axial direction of the second outer pipe 22B, and the first angle θ1 and the second angle θ2 are leaned to different sides of the axial direction; thus the two fork structures 211B, 221B can apply opposite out-tension forces F1, F2 to the tail portion 12 and the head portion 11, respectively. Thereupon, while in rotating the first outer pipe 21B to shrink the bigger diameter of the belt 10, the belt 10 can be kept contact with the first outer pipe 21B and the second outer pipe 22B. More specifically, during the process for the belt 10 to tighten the cervix, the plug holes 121, 111 of the belt 10 can kept holding the corresponding fork structures 211B, 221B of the first outer pipe 21B and the second outer pipe 22B, respectively.

Referring now to FIGS. 21A-21C, FIGS. 22A-22C and FIG. 23, the belt 10A includes a head portion 11A, a tail portion 12A and a middle portion 13A. The head portion 11A has a head-end plug hole 111A and a head-end through hole 112A. The head-end through hole 112A has an inner teeth structure 113A. The tail portion 12A has a tail-end plug hole 121A. The middle portion 13A has at least one section with both opposing lateral sides furnished with individual outer teeth structures 131A, 132A, in correspondence with the inner teeth structures 113A, 114A, respectively. In addition, the belt 10A further includes a plurality of bumps 14A protrusive individually on a surface of the middle portion 13A. Then, lead the tail portion 12A to pierce the head-end through hole 112A of the head portion 11A, by having the opposing outer teeth structures 131A, 132A of the middle portion 13A to engage the corresponding inner teeth structures 113A, 114A, as shown in FIG. 23. Thereupon, the belt 10A can be reformed into the adjustable ring as shown in FIG. 18. At this stage, the plurality of bumps 14A are located inside the adjustable ring. As described above, the instrument 20 or 20A of FIG. 1 or FIG. 4, respectively, can be applied to adjust the belt 10A.

Referring now to FIGS. 24A-24C, the belt 10B of this embodiment is derived from the belt 10 of FIGS. 15A-15C. As shown, the belt 10B includes a head portion 11B, a tail portion 12B and a middle portion 13B. The head portion 11B has a head-end plug hole 111B and a head-end through hole 112B. The head-end through hole 112B has an inner teeth structure 113B, 114B. The tail portion 12B has a tail-end plug hole 121B. The middle portion 13B has at least one section with both opposing lateral sides furnished with individual outer teeth structures 131B, 132B, in correspondence with the inner teeth structures 113B, 114B, respectively. Between the two outer teeth structures 131B, 132B in the middle portion 13B, an elastic structure 133B is disposed. The elastic structure 133B is formed by a plurality of arc-shaped perforations extending lengthwise to provide a compressible space between the two outer teeth structures 131B, 132B, so as thereby to reduce the resistance at the middle portion 13B while in tensioning the head portion 11B. In addition, the belt 10B further includes a plurality of bumps 14B protrusive individually on a surface of the head portion 11B and the middle portion 13B. As shown, in this embodiment, the head portion 11B has one said bump 14B. According to this disclosure, it is not necessary to have bumps 14B in the head portion 12B. Then, lead the tail portion 12B to pierce the head-end through hole 112B of the head portion 11B, by having the opposing outer teeth structures 131B, 132B of the middle portion 13B to engage the corresponding inner teeth structures 113B, 114B, respectively, as shown in FIG. 17. Thereupon, the belt 10B can be reformed into the adjustable ring as shown in FIG. 18. At this stage, the plurality of bumps 14B are located inside the adjustable ring.

In this embodiment, other features include that, by locating the head-end plug hole 111B away from the side of the head portion 11B having the bumps 14B, the belt 10B can properly tighten the cervix without substantial position bias after the fork structure 221B is retrieved from the head-end plug hole 111. Similarly, in FIGS. 15A-15C and FIGS. 21A-21C, the head-end plug holes 111, 111A of the belts 10, 10A can be relocated to another side of the head portions 11, 11A, respectively. In addition, in this embodiment, a plurality of perforated portions 15B located between the middle portion 13B and the head portion 11B are included to adjust the entire stiffness of the belt 10B, such that the belt 10 of FIG. 18 can be kept in a circle shape by waiving possible weakness caused by the elastic structure 133B.

Referring now to FIGS. 25A-25F, different stages of operation of the embodiment of FIG. 1 upon a cervix inside a vagina are shown orderly. The operator, an surgeon for example, firstly applies the instrument 20 to the belt 10 by inserting. Then, a duck-billed speculum (not shown in the figure) is used to expand the vagina 90 so as to allow the instrument 20 to place the belt 10 to a place in the vagina 90 by approaching the cervix 91.

Referring now to FIG. 25A, one end of the instrument that has the belt is sent into the vagina 90, and then the second inner pipe 24 is pushed to open the claw mechanism 25 and to contact a periphery of the cervix 91.

Referring now to FIG. 25B, the second inner pipe 24 is pulled to close the claw mechanism 25 for clamping at the periphery of the cervix 91.

Referring now to FIG. 25C, both the first outer pipe 21 and the second outer pipe 22 are pushed forward so as to have the belt 10 to move toward the cervix 91 and to reach the periphery of the cervix 91 by surpassing the claw mechanism 25. Then, the first outer pipe 21 is rotated to have the belt 10 to tie the cervix 91 at the periphery thereof. Refer back to FIG. 18 and the related description for a method to adjust the inner diameter of the belt 10. By having the bumps 14 to bite the cervix 91, the fixation of the belt lo on the cervix 91 can be further ensured.

Referring now to FIG. 25D, both the first outer pipe 21 and the second outer pipe 22 are pulled outward so as to separate the first outer pipe 21 and the second outer pipe 22 away from the belt 10. Then, the belt 10 can sleeve the cervix 91 at the periphery thereof. It should be noted that, at this time, the claw mechanism 25 still clamps the cervix 91 at the periphery thereof.

Referring now to FIG. 25E, the second inner pipe 24 is pushed to open the claw mechanism 25, and so the cervix 91 is released from the claw mechanism 25.

Referring now to FIG. 25F, the first inner pipe 23 and the second inner pipe 24 are pulled back to be stored into the first outer pipe 21 and the second outer pipe 22. Then, the entire instrument 20 is retrieved away from the vagina 90. Upon such an operation, the belt 10 can tie the cervix 91 in a sleeving manner.

Referring now to FIGS. 26A-26F, different stages of operation of the embodiment of FIG. 7 upon a cervix inside a vagina are shown orderly. The operator, an surgeon for example, firstly applies the instrument 20B to the belt 10B by inserting. Then, a duck-billed speculum (not shown in the figure) is used to expand the vagina 90 so as to allow the instrument 20B to place the belt 10B to a place in the vagina 90 by approaching the cervix 91.

Referring now to FIG. 26A, one end of the instrument 20B that has the belt 10B is sent into the vagina 90, and then the first inner pipe 23B is pulled away from the claw mechanism 25B, so as to retrieve the second handle 231B away from the positioning slot 222B and the round hole 223B as shown in FIG. 11. Thereupon, the claw mechanism 25B can be opened to contact a periphery of the cervix 91.

Referring now to FIG. 26B, the first inner pipe 23B is pushed to close the claw mechanism 25B for clamping at the periphery of the cervix 91, by applying the second handle 231B.

Referring now to FIG. 26C, both the second outer pipe 22B and the first outer pipe 21B are simultaneously pushed forward so as to have the belt 10B to move toward the cervix 91 and to reach the periphery of the cervix 91 by surpassing the claw mechanism 25B. Then, the first outer pipe 21B is rotated to have the belt 10B to tie the cervix 91 at the periphery thereof.

Referring now to FIG. 26D, apply the first handle 212B to pull outward both the first outer pipe 21B and the second outer pipe 22B so as to separate both the first outer pipe 21B and the second outer pipe 22B away from the belt 10B. Then, the belt 10B can sleeve the cervix 91 at the periphery thereof. It should be noted that, at this time, the claw mechanism 25B still clamps the cervix 91 at the periphery thereof.

Referring now to FIG. 25E, apply the second handle 231B to pull the first inner pipe 23B so as to open the claw mechanism 25B, and so the cervix 91 is released from the claw mechanism 25B.

Referring now to FIG. 26F, the entire instrument 20B is retrieved away from the vagina 90. Upon such an operation, the belt 10B can tie the cervix 91 in a sleeving manner.

It is noted that the aforesaid operation can be arbitrarily applied to the instrument 20 of FIG. 1 and the belt 10 of FIG. 15A, the instrument 20A of FIG. 4 and the belt 10A of FIG. 21A, and the instrument 20B of FIG. 7 and the belt 10B of FIG. 24A. No matter what style of the instrument or belt is, the operation is the same.

As described above, by providing a simple-structured and easy-operated device, instrument and belt to tie a cervix of a pregnant woman for avoiding preterm birth that can be applied clinically without a surgery, an anesthetic process and even hospitalization in accordance with this disclosure, the acceptability by pregnant women would be increased, and the occurrence rate of the preterm birth would be significantly reduced.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A device for tying a cervix, comprising: a belt for tying the cervix; and an instrument, applied to tie the belt onto the cervix, including: a first outer pipe and a second outer pipe being rotatable to each other; and two fork structures, connected individually to corresponding axial ends of the first outer pipe and the second outer pipe, respectively, each of the two fork structures detachably inserted into the belt, further including: a claw mechanism; and a first inner pipe and a second inner pipe, one of the first inner pipe and the second inner pipe being connected with the claw mechanism, the first inner pipe and the second inner pipe being movable to each other, the two fork structures being located exteriorly to the claw mechanism and able to move back and forth axially about the claw mechanism, wherein the second outer pipe is furnished with a second-outer-pipe sliding slot penetrating and extending axially along the second outer pipe by a predetermined length, the first inner pipe is furnished with a first-inner-pipe sliding slot penetrating and extending axially along the first inner pipe by another predetermined length, the second-outer-pipe sliding slot corresponds to the first-inner-pipe sliding slot, and a sliding node is movable inside the second-outer-pipe sliding slot and the first-inner-pipe sliding.

2. The device of claim 1, wherein the first inner pipe, the second inner pipe, the first outer pipe and the second outer pipe are co-axial.

3. The device of claim 1, wherein a first angle is formed by a lateral edge of the fork structure of the first outer pipe with respect to an axial direction of the first outer pipe, a second angle is formed by a lateral edge of the fork structure of the second outer pipe with respect to an axial direction of the second outer pipe, and the first angle and the second angle are leaned to different directions.

4. The device of claim 3, wherein both the first angle and the second angle are in a range of 1-45 degrees.

5. The device of claim 1, wherein the second inner pipe has a hand grip furnished to an axial end thereof away from the claw mechanism.

6. The device of claim 5, wherein the hand grip has a central through hole extending in an axial direction of the second inner pipe and connecting spatially to an interior of the second inner pipe, and the central through hole is provided to be plugged by a lighting device.

7. The device of claim 6, wherein the lighting device includes an elongated light source and a control box detachably connected with the light source for energizing and controlling the light source.

8. The device of claim 1, wherein the first outer pipe has a first handle.

9. The device of claim 1, wherein a step ring is constructed fixedly to an outer surface of the second outer pipe, and the first outer pipe is mounted between the step ring and the fork structure of the second outer pipe, such that axial movement of the first outer pipe is limited but rotational movement thereof is avowed.

10. The device of claim 1, wherein the first inner pipe has a second handle.

11. The device of claim 10, wherein the second outer pipe has a positioning slot located at another axial end thereof opposite to the axial end having the fork structure, the positioning slot extends axially along the second outer pipe by a predetermined length and connects spatially to a round hole, and a diameter of the round hole is equal to or larger than an outer diameter of the second handle.

12. The device of claim 11, wherein a width of the positioning slot is less than the outer diameter of the second handle, and the second outer pipe further has a pair of axial slits to sandwich the positioning slot lengthwise.

13. The device of claim 1, wherein a top of the sliding node does not interfere with an inner wall of the first outer pipe.

14. The device of claim 1, wherein the claw mechanism of the instrument is disposed at an axial end of the first inner pipe, the claw mechanism and the second inner pipe being connected through a gear and a corresponding rack.

15. The device of claim 1, wherein the claw mechanism includes a cantilever structure extending outwards from the second inner pipe.

16. The device of claim 1, wherein the belt includes: a head portion, having a head-end plug hole and a head-end through hole, the head-end through hole having thereinside an inner teeth structure; a tail portion, having a tail-end plug hole; and a middle portion, located between the head portion and the tail portion, having at least one section thereof with two opposing lateral sides to provide individual outer teeth structures to pair the inner teeth structure, the two fork structures of the instrument detachably inserted into the head-end plug hole and the tail-end plug hole, respectively.

17. The device of claim 16, wherein the belt further includes an elastic structure located between the two outer teeth structures of the middle portion.

18. The device of claim 16, wherein the belt further includes a plurality of bumps protrusive on a surface of the belt.

19. The device of claim 18, wherein the head-end plug hole is located to a side of the head portion away from the plurality of bumps.

20. The device of claim 16, further including a plurality of perforated portions between the middle portion and the head portion.

21. An instrument, comprising: a first outer pipe and a second outer pipe, the first outer pipe and the second outer pipe being rotatable to each other; and two fork structures, connecting individually with corresponding axial ends of the first outer pipe and the second outer pipe, respectively, the two fork structures inserted into a belt detachably, further including: a claw mechanism; and a first inner pipe and a second inner pipe, one of the first inner pipe and the second inner pipe being connected with the claw mechanism, the first inner pipe and the second inner pipe being movable to each other, the two fork structures being located exteriorly to the claw mechanism and able to move back and forth axially about the claw mechanism, wherein the second outer pipe is furnished with a second-outer-pipe sliding slot penetrating and extending axially along the second outer pipe by a predetermined length, the first inner pipe is furnished with a first-inner-pipe sliding slot penetrating and extending axially along the first inner pipe by another predetermined length, the second-outer-pipe sliding slot corresponds to the first-inner-pipe sliding slot, and a sliding node is movable inside the second-outer-pipe sliding slot and the first-inner-pipe sliding.

22. The instrument of claim 21, wherein the first inner pipe, the second inner pipe, the first outer pipe and the second outer pipe are co-axial.

23. The instrument of claim 21, wherein a first angle is formed by a lateral edge of the fork structure of the first outer pipe with respect to an axial direction of the first outer pipe, a second angle is formed by a lateral edge of the fork structure of the second outer pipe with respect to an axial direction of the second outer pipe, and the first angle and the second angle are leaned to different directions.

24. The instrument of claim 23, wherein both the first angle and the second angle are in a range of 1-45 degrees.

25. The instrument of claim 21, wherein the second inner pipe has a hand grip furnished to an axial end thereof away from the claw mechanism.

26. The instrument of claim 25, wherein the hand grip has a central through hole extending in an axial direction of the second inner pipe and connecting spatially to an interior of the second inner pipe, and the central through hole is provided to be plugged by a lighting device.

27. The instrument of claim 26, wherein the lighting device includes an elongated light source and a control box detachably connected with the light source for energizing and controlling the light source.

28. The instrument of claim 21, wherein the first outer pipe has a first handle.

29. The instrument of claim 21, wherein a step ring is constructed fixedly to an outer surface of the second outer pipe, and the first outer pipe is mounted between the step ring and the fork structure of the second outer pipe, such that axial movement of the first outer pipe is limited but rotational movement thereof is allowed.

30. The instrument of claim 21, wherein the first inner pipe has a second handle.

31. The instrument of claim 30, wherein the second outer pipe has a positioning slot located at another axial end thereof opposite to the axial end having the fork structure, the positioning slot extends axially along the second outer pipe by a predetermined length to connect spatially a round hole, and a diameter of the round hole is equal to or larger than an outer diameter of the second handle.

32. The instrument of claim 31, wherein a width of the positioning slot is less than the outer diameter of the second handle, and the second outer pipe further has a pair of axial slits to sandwich the positioning slot lengthwise.

33. The instrument of claim 21, wherein a top of the sliding node does not interfere with an inner wall of the first outer pipe.

34. The instrument of claim 21, wherein the claw mechanism of the instrument is disposed at an axial end of the first inner pipe, the claw mechanism and the second inner pipe being connected through a gear and a corresponding rack.

35. The instrument of claim 21, wherein the claw mechanism includes a cantilever structure extending outwards from the second inner pipe.

* * * * *